United States Patent
Wu et al.

(10) Patent No.: US 8,742,756 B2
(45) Date of Patent: Jun. 3, 2014

(54) MAGNETIC RESONANCE IMAGING APPARATUS AND METHOD OF ASSISTING SETTING OF IMAGING PARAMETER

(75) Inventors: Binrong Wu, Tokyo (JP); Hiroyuki Itagaki, Tokyo (JP); Takashi Nishihara, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 696 days.

(21) Appl. No.: 12/996,216

(22) PCT Filed: Jun. 9, 2009

(86) PCT No.: PCT/JP2009/060501
§ 371 (c)(1),
(2), (4) Date: Dec. 3, 2010

(87) PCT Pub. No.: WO2009/151041
PCT Pub. Date: Dec. 17, 2009

(65) Prior Publication Data
US 2011/0074418 A1    Mar. 31, 2011

(30) Foreign Application Priority Data
Jun. 9, 2008 (JP) .................... 2008-150646

(51) Int. Cl.
*G01V 3/00* (2006.01)
*G01R 33/48* (2006.01)
(52) U.S. Cl.
USPC ............ 324/309; 324/307; 324/318; 600/410
(58) Field of Classification Search
USPC .................... 324/300–322; 600/407–465; 382/128–131
See application file for complete search history.

(56) References Cited

U.S. PATENT DOCUMENTS

| 7,081,750 B1* | 7/2006 | Zhang | 324/309 |
| 2003/0095150 A1* | 5/2003 | Trevino et al. | 345/810 |
| 2007/0098240 A1 | 5/2007 | Takayama | |
| 2009/0030302 A1* | 1/2009 | Taniguchi et al. | 600/410 |
| 2009/0278535 A1* | 11/2009 | Takizawa et al. | 324/309 |
| 2013/0113486 A1* | 5/2013 | Imamura et al. | 324/322 |
| 2013/0225976 A1* | 8/2013 | MIYAZAKI et al. | 600/413 |

FOREIGN PATENT DOCUMENTS

| JP | 5-176911 | 7/1993 |
| JP | 11-47109 | 2/1999 |
| JP | 2003-210433 | 7/2003 |
| JP | 2007-111112 | 5/2007 |

(Continued)

OTHER PUBLICATIONS

International Search Report in PCT/JP2009/060501.

*Primary Examiner* — Melissa Koval
*Assistant Examiner* — Emily Chan
(74) *Attorney, Agent, or Firm* — Cooper & Dunham LLP

(57) ABSTRACT

An object is to enhance usability of parameter check when an imaging parameter is changed in multistation imaging, and easily obtain a desired image with high quality. In the multistation imaging, it is determined in a lump before imaging whether an image having desired quality is obtained by using the changed value of the imaging parameter, and the result is presented to an operator. The determination is executed in the order of "possible or impossible" determination of execution of imaging itself and "possible or impossible" determination of combination of obtained images. When it is determined that it is impossible to execute the imaging itself, the determination processing is finished. At this time, a recommended value may be presented.

7 Claims, 19 Drawing Sheets

(56) References Cited

FOREIGN PATENT DOCUMENTS

| | | |
|---|---|---|
| JP | 2007-181659 | 7/2007 |
| WO | WO2006/117922 A1 | 11/2006 |
| WO | WO2006/134958 A1 | 12/2006 |
| WO | WO2006/135003 A1 | 12/2006 |

* cited by examiner

FIG. 7
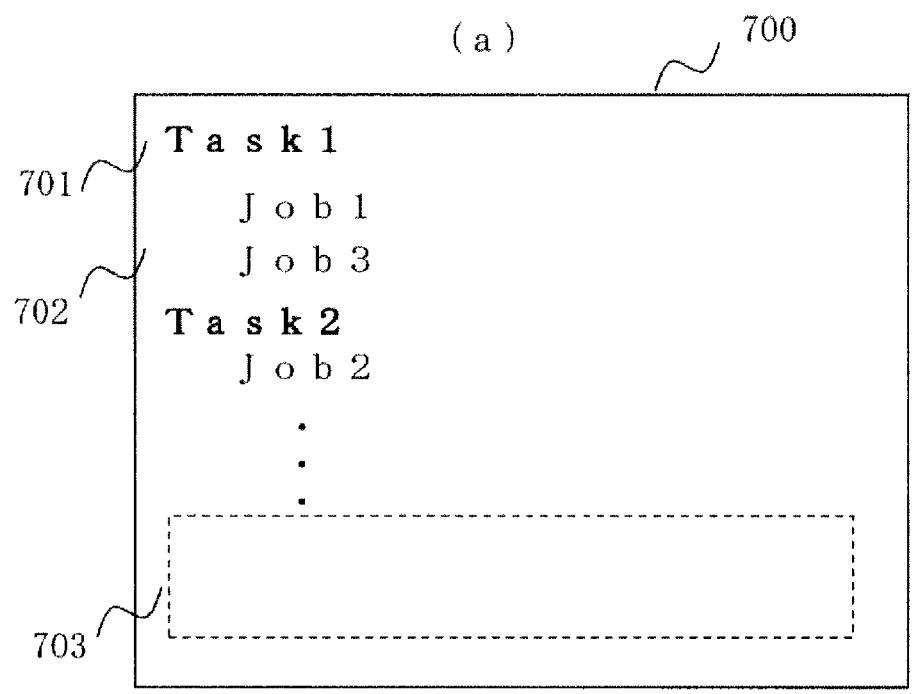
(a)
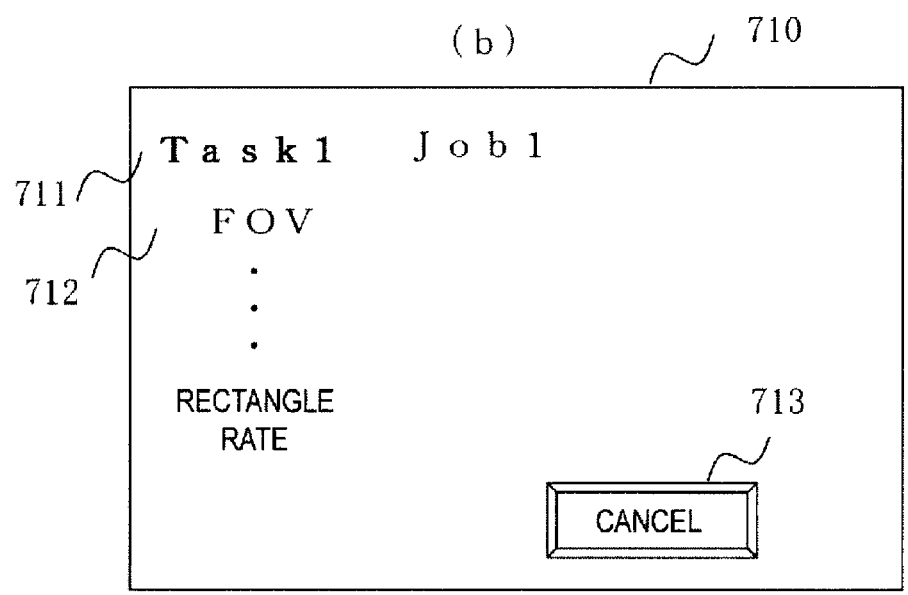
(b)

FIG. 15
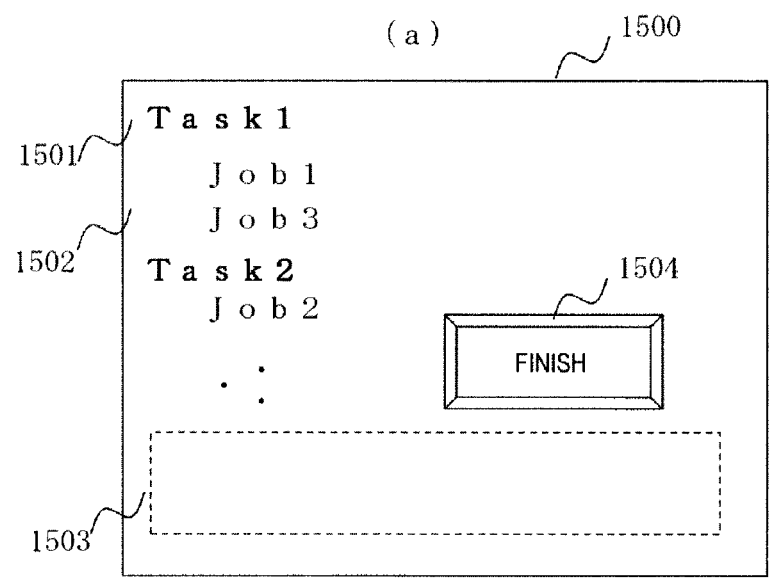
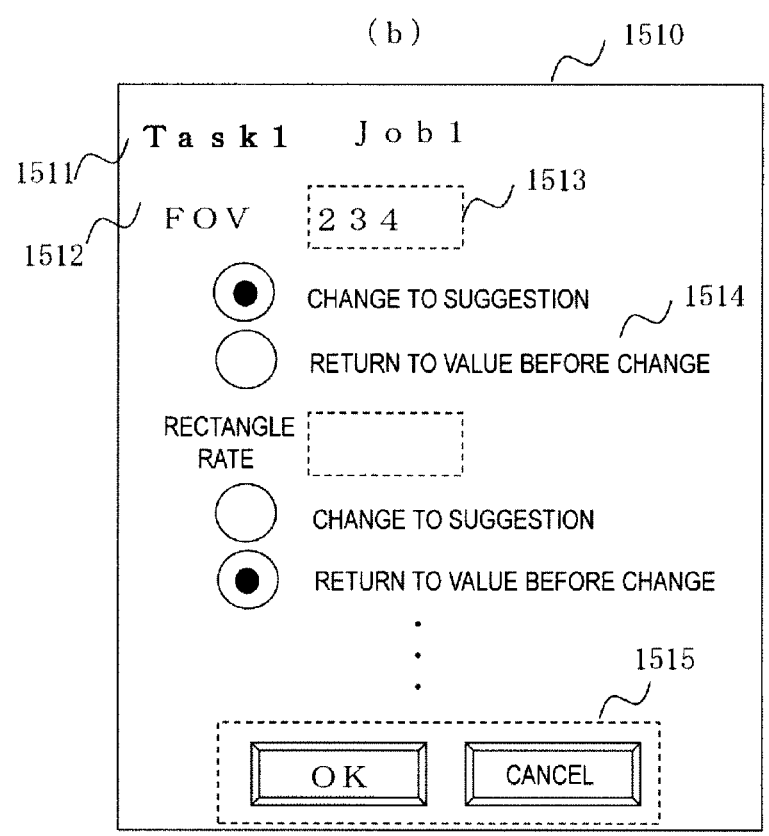

MAGNETIC RESONANCE IMAGING APPARATUS AND METHOD OF ASSISTING SETTING OF IMAGING PARAMETER

TECHNICAL FIELD

The present invention relates to a multistation imaging technique of performing imaging based on step movement in a magnetic resonance imaging apparatus. Particularly, the present invention relates to a parameter setting assisting technique in multistation imaging.

BACKGROUND ART

The magnetic resonance imaging (MRI) apparatus measures a nuclear magnetic resonance (hereinafter referred to as "NMR") signal from protons in an examinee and picks up images of (images) a density distribution, a relaxation time distribution, etc. of protons. Recently, whole body imaging (whole body MRI) for repeatedly moving a bed on which an examinee is put, picking up MRI images of the whole body of the examinee (hereinafter, whole body images) and performing screening examination, etc. has recently commanded interest. In the multistation imaging in which a bed is moved stepwise to pick up a whole body image, an examinee is imaged in conformity with the movement of the bed while the examinee is partitioned into plural stations (imaging areas), and thus-obtained images are combined with one another to create a whole body image. During the image pickup operation at each station, the bed is kept under the stop state, and the bed is moved between the imaging operations.

When some processing is executed on images obtained in the multistation imaging, imaging parameters necessary for the processing for images obtained at each station are required to be set to the same parameters. For example, there is known a technique of assisting that imaging parameters for projection processing are set to be identical every image at each station when the projection processing is executed (for example, see Patent Document 1).

Furthermore, in order to obtain information contributing diagnosis at each station of the multistation imaging, imaging is executed by using plural imaging sequences such as T1 emphasis, T2 emphasis, diffusion emphasis, etc. (multistation/multisequence imaging) in some cases.

In the multisequence imaging, it is generally necessary to set respective imaging parameters for plural imaging sequences while achieving consistence with other sequences. There is known a technique of assisting setting of the imaging parameters for the multisequence imaging as described above (for example, see Patent Document 2). In this case, input screens for the imaging parameters for the plural imaging sequences are provided on the same screen so that the imaging parameters for the respective imaging sequences can be input without switching the screen, thereby enhancing operationality.

PRIOR ART DOCUMENT

Patent Document

Patent Document 1: JP-A-2007-181659
Patent Document 2: JP-A-11-47109

SUMMARY OF THE INVENTION

Problem to be Solved by the Invention

As described above, a technique for assisting the setting of the imaging parameters is known for each of the multisequence imaging and the multistation imaging. However, it has not been checked whether an image having desired image quality can be obtained by using the thus-set imaging parameters. It is needless to say that it has been hitherto checked for one imaging sequence whether imaging based on set imaging parameters is possible or not. However, in the multisequence/multistation imaging, the number of imaging sequences executed to obtain all images is large, and thus an excessive load is imposed on an operator when this method is directly applied. Furthermore, in the multistation imaging, images of respective stations are combined with one another. It cannot be confirmed by checking possibility or impossibility of imaging for one imaging sequence whether the combination is possible or not or whether the quality of combined images is good or not. Accordingly, in the multistation imaging, it is not easy to change the values of temporarily set imaging parameters and obtain a desired image having high quality.

The present invention has been implemented in view of the foregoing situation, and has an object to enhance usability of parameter check when imaging parameters are changed in multistation imaging, and easily obtain a desired image with high quality.

Means of Solving the Problems

The present invention determines in a lump before imaging whether an image having desired quality is obtained by using the values of changed imaging parameters in multistation imaging, and presents a result to an operator. This determination is executed in the order of determining as to whether it is possible to execute imaging itself or not and then determining whether obtained images can be combined or not.

Specifically, a magnetic resonance imaging apparatus for performing multistation imaging is characterized by comprising: imaging managing unit that manages imaging executed at each station of the multistation imaging; an input unit that accepts an input of an imaging parameter value used for the imaging concerned every imaging managed by the imaging managing unit; an imaging "possible or impossible" determining unit that determines before start of the multistation imaging whether a new imaging parameter value input through the input unit is proper or not with respect to each imaging in which the new imaging parameter is input through the input unit; and an error display unit that displays, as an error, information for enabling specification of imaging having an imaging parameter value determined to be improper by the imaging "possible or impossible" determining unit and the imaging parameter value determined to be improper.

Furthermore, an imaging parameter setting assisting method for setting an imaging parameter value used to perform multistation imaging before the multistation imaging is executed is characterized by comprising: an input accepting step that accepts an input of a desired imaging parameter value; an imaging specifying step that specifies, from all imaging executed in the multistation imaging, imaging in which an imaging parameter value is newly input; an imaging "possible or impossible" determining step that determines whether the newly input imaging parameter value is proper or not with respect to each imaging specified in the imaging specifying step; and a display step that displays, as an error, information for enabling specification of imaging having an imaging parameter value determined to be improper in the imaging "possible or impossible" determining step and the imaging parameter value determined to be improper.

Advantage of the Invention

According to the present invention, in the multistation imaging, usability of parameter check when the imaging parameter is changed is enhanced, and a desired image can be easily obtained with high quality.

BRIEF DESCRIPTION OF THE DRAWINGS

FIG. 7 shows an example of an error display screen of the first embodiment.

FIG. 15 shows an example of an error suggestion display screen of the second embodiment.

MODE FOR CARRYING OUT THE INVENTION

First Embodiment

Figure 1:
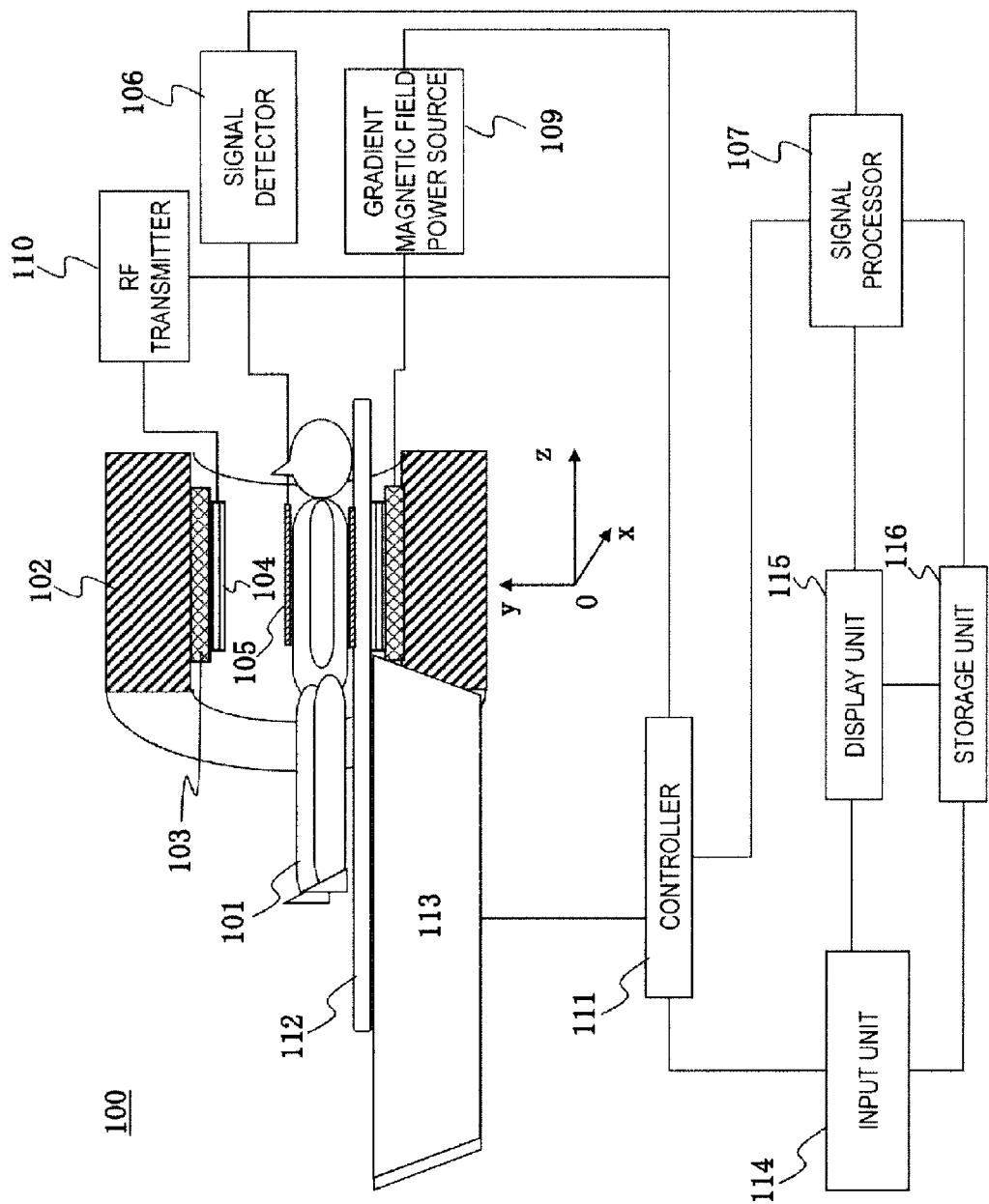
FIG. 1 is a functional block diagram of an MRI apparatus according to a first embodiment.

Embodiments of the present invention will be described with reference to the drawings. The elements having the same functions are represented by the same reference numerals in all figures showing the embodiments of the present invention, and the repetitive description thereof is omitted. An embodiment of an MRI apparatus will be described with reference to the drawings.

FIG. 1 is a functional block diagram showing a magnetic resonance imaging (MRI) apparatus 100 according to an embodiment. As shown in FIG. 1, the magnetic resonance imaging apparatus 100 according to the embodiment has a bed 112 on which an examinee 101 is put, a magnet 102 for generating magnetostatic field, a gradient magnetic field coil 103 for generating gradient magnetic field in the space, an RF transmission coil 104 for generating high-frequency magnetic field in this area, an RF reception coil 105 for receiving a nuclear magnetic resonance (MR) signal generated by the examinee 101, a signal detector 106 for detecting the MR signal detected by the RF reception coil 105, a signal processor 107 for processing the MR signal detected by the signal detector 106 and performing the control of the whole MRI apparatus 100 and various kinds of information processing, a gradient magnetic field power source 109 for feeding current to drive the gradient magnetic field coil 103, an RF transmitter 110 for transmitting a signal for making the RF transmission coil 104 generate high-frequency magnetic field, a controller 111 for controlling the whole of the system according to an imaging sequence, the bed 112 on which an examinee is put, a bed driving unit 113 for driving the bed 112 under the control of the controller 111, an input unit 114 and a display unit 115 serving as input and output interfaces, and a storage unit 116 for storing various kinds of data necessary for the processing of the signal processor 107 and data obtained through the processing.

The gradient magnetic field coil 103 includes gradient magnetic field coils of three directions of x, y, z. Current is supplied form the gradient magnetic field power source 109 to the gradient magnetic field coil 103 in accordance with a signal from the controller 111 to generate gradient magnetic fields which are mutually orthogonal to each other. A slice selection gradient magnetic field, a phase encode gradient magnetic field and a reading gradient magnetic field are set in any directions by the respective gradient magnetic fields to allocate positional information to each MR signal. Furthermore, in this embodiment, the bed driving unit 113 controls at least the movement of the bed 112 in the body axis direction (z direction) in accordance with a control signal supplied from the controller 111.

The MRI apparatus 100 of this embodiment performs multistation/multisequence imaging in which imaging is executed at plural times at each station of the multistation imaging. When imaging parameters used for each imaging sequence at each station are changed, the "possible or impossible" of the change is determined. In order to implement these processing, the signal processor 107 of this embodiment has a sequence managing unit, an imaging unit, an image reconstructing unit and a parameter check unit.

Figure 2:
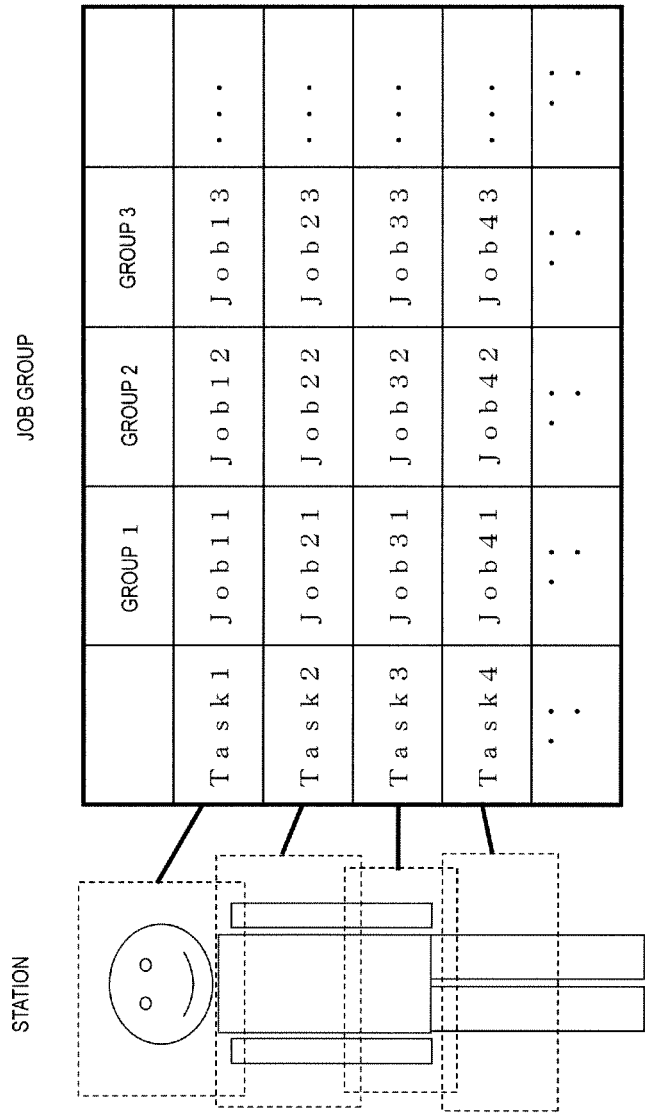
FIG. 2 is an association diagram of Job, Task and group of the first embodiment.

The sequence managing unit manages an imaging sequence (Job) executed in one multistation/multisequence imaging operation by a sequence managing table. In this embodiment, a job group of each station is called as a Task, Job groups of all Tasks, that is, all Job groups executed in one multistation/multisequence imaging operation are called as an examination. Furthermore, the multistation/multisequence imaging operation of this embodiment contains an imaging operation of combining images picked up at each station to obtain one image in the moving direction of the bed 112. A Job group for combining the obtained images is called as Group every combination unit. The association of Job, Task and Group is shown in FIG. 2.

Figure 3:
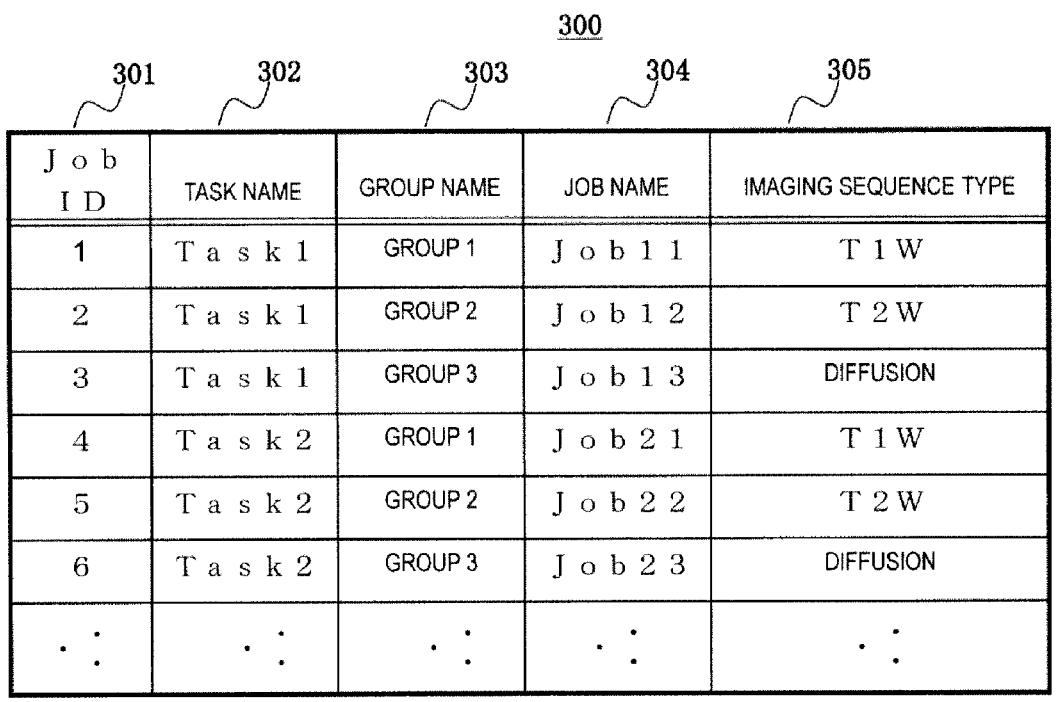
FIG. 3 shows an example of a sequence managing table according to the first embodiment.

The sequence managing unit of this embodiment manages the association of Task and Group of these Job groups and the type of the imaging sequence being used in the sequence managing table while allocating Job IDs to them. FIG. 3 shows an example of a sequence managing table 300 according to the embodiment. As shown in FIG. 3, Job ID 301, Task name 302, group name 303, Job name 304 and imaging sequence type 305 are stored in the sequence managing table 300 of this embodiment. The sequence managing table 300 is stored in the storage unit 116.

The imaging unit controls the controller 111 every Job according to the examination content to be managed by the sequence managing unit and executes imaging. The imaging unit transmits a command and a signal to the controller 111 according to a predetermined control time chart (pulse sequence), and controls the operations of the gradient magnetic field power source 109, the RF transmitter 110 and the signal detector 106 to execute each Job. Set imaging parameters are used when Job is executed. In this embodiment, in order to perform the multistation imaging, the imaging unit makes the controller 111 control the bed driving unit 113 so that the bed 112 is moved by a predetermined distance in conformity with the execution of the imaging.

The image reconstructing unit subjects the signal detected by the signal detector 106 to processing such as FFT (Fast Fourier Transform) or the like to reconstruct an image by using a well-known technique. In this embodiment, in order to perform the multistation imaging, the images of the respective stations obtained from Job of the same group are combined with one another after the reconstruction, and an image in a desired range such as a whole body or the like is obtained.

The parameter check unit executes parameter check processing of determining whether the imaging parameters accepted from a user through the input unit 114 are proper or not, and presenting the result to the user. The parameter check unit has an imaging "possible or impossible" determining unit for determining from the viewpoint of the possibility or impossibility of imaging whether the imaging parameters are proper or not, and a combination "possible or impossible" determining unit for determining it from the viewpoint of the "possible or impossible" determination of the combination of reconstructed images. When receiving an instruction from the user or when a preset imaging parameter is changed, the parameter check processing is executed in a lump with respect to all Jobs in which the imaging parameter is changed before the multistation/multisequence imaging is started. Furthermore, the "proper or not" determination of the combination "possible or impossible" determining unit is executed after it is determined by the imaging "possible or impossible" determining unit that the imaging is possible.

Various kinds of data used for the processing of each function unit described above, for example, various kinds of imaging sequences which can be executed in the MRI apparatus 100 according to this embodiment, the types of imaging parameters to be set in each imaging sequence, permissible ranges of the respective imaging parameters, etc. are stored in the storage unit 116 in advance. A table in which the permissible range of each imaging parameter is stored is called as a parameter managing table. Furthermore, various kinds of data generated during the processing of each function unit are also stored in the storage unit 116.

Furthermore, the values of the imaging parameters of each Job are managed in association with Job IDs 301. The value of each imaging parameter before changed is called as an initial value, and the value of an imaging parameter which is input to be changed from the user is called as a changed value. Furthermore, out of the initial values of the imaging parameters, a value group of initial values to which changed values are input and thus which are replaced by the changed values is called as a changed value set. The changed value set is temporarily stored in a file in the storage unit 116 after input, subjected to the following parameter check processing, and then replaced by the initial value upon reception of an instruction from the user. The imaging unit executes imaging by using the initial value.

The details of the parameter check processing of the parameter check unit according to the embodiment will be described.

Figure 4:
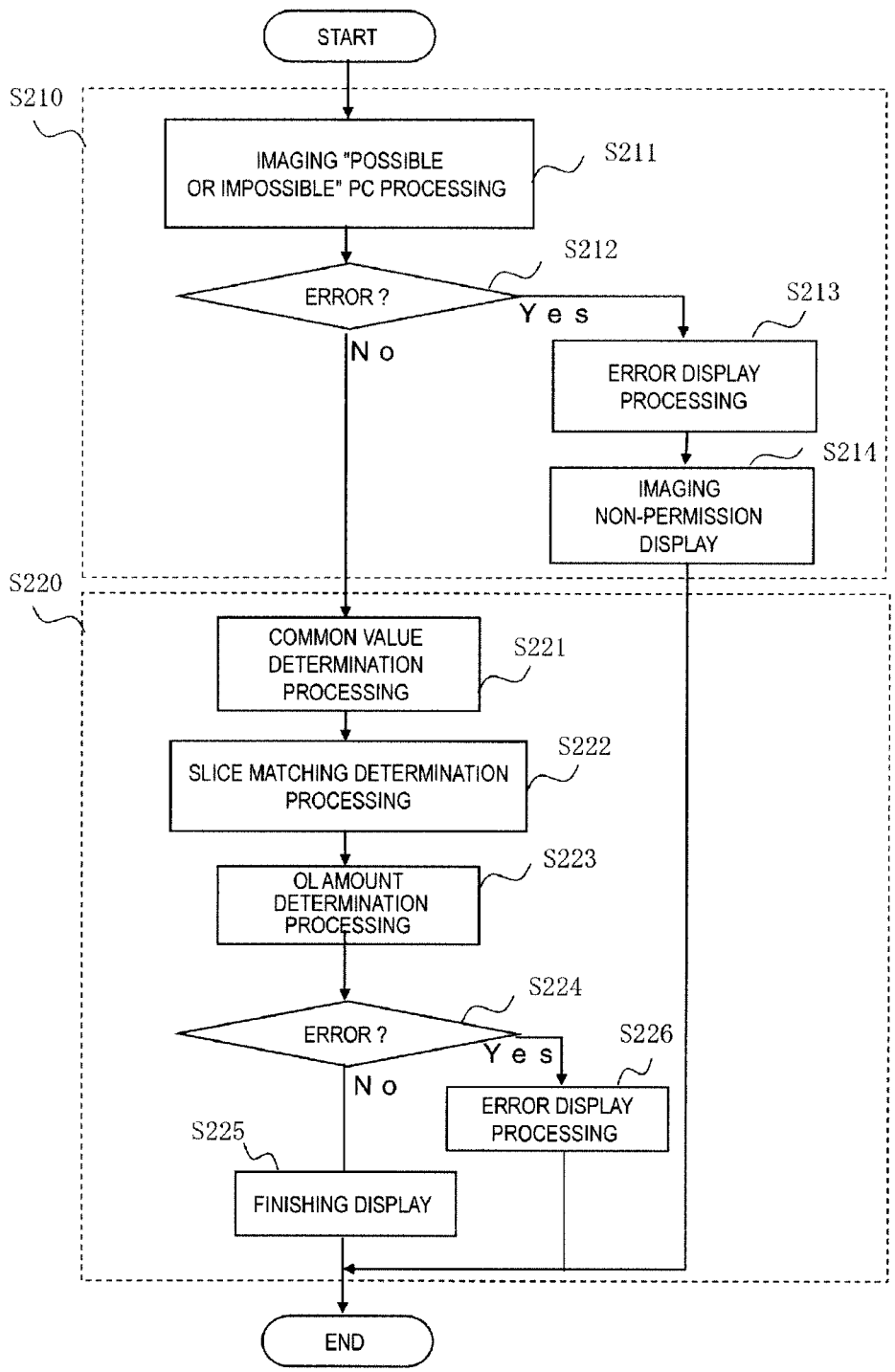
FIG. 4 is a processing flow of parameter check processing according to the first embodiment.

FIG. 4 is a processing flow of the parameter check processing according to the embodiment. The following description will be made on the assumption that the processing is started when an instruction of changing imaging parameters is accepted from the user. This processing may be constructed so that it starts upon acceptance of an instruction of starting the parameter check processing from the user.

The user inputs an imaging parameter to be changed and a changed value thereof through the input unit 114 together with Job for changing the imaging parameter, and instructs the change when finishes an input of the changed value of a desired imaging parameter of desired Job. Upon acceptance of an instruction of the change from the user through the input unit 114, the imaging "possible or impossible" determining unit executes the imaging "possible or impossible" determination processing of determining whether the imaging is possible on the basis of the accepted changed value (step S210). In this case, when the instruction of the change is accepted, the imaging "possible or impossible" determining unit inquires to the sequence managing unit, extracts a Job group in which the imaging parameter is changed, and executes the imaging "possible or impossible" parameter check (PC) processing of determining possibility or impossibility of the imaging for each Job (step S211). Here, in the imaging "possible or impossible" PC processing, it is determined whether the changed value is within a predetermined range or not (step S212). When there is an imaging parameter out of the range, an error is set.

When there is an error, the imaging "possible or impossible" determining unit executes error display processing (step S213), does not permit the imaging, displays this fact to the user (step S214), and finishes the parameter check processing. Presentation of no permission of the imaging is implemented by using an imaging non-permission flag, for example. On the other hand, when there is no error in step S212, it is transmitted to the combination "possible or impossible" determining unit that the imaging "possible or impossible" determination processing is finished.

The combination "possible or impossible" determining unit which receives a notification from the imaging "possible or impossible" determining unit executes the combination "possible or impossible" determination processing (step S220). In the combination "possible or impossible" determination processing are executed common value determination processing (step S221) for determining whether a predetermined imaging parameter has the same value in a predetermined Job (step S221), slice matching determination processing for determining whether there is slice matching between Jobs within a group in multislice imaging or the like (step S222) and OL amount determination processing (step S223) for determining whether there is an overlap (OL) amount at which images between stations to be combined can be combined with one another.

In all the processing, when there is no error and a combination possibility result is obtained (step S224), an end display is made (step S225), and the parameter check processing is finished. In the end display, the combination "possible or impossible" determining unit displays no error and a screen for accepting a final instruction of replacing the initial value with the changed value. In this case, the end display may not be made, and only the processing of replacing the initial value with the changed value may be executed. On the other hand, in step S224, when a combination impossibility result is obtained in any processing, the error display (step S226) is made, and the parameter check processing is finished. The combination "possible or impossible" determining unit of this embodiment permits the imaging even when there is an error. Accordingly, in the error display, the combination "possible or impossible" determining unit displays a reason why an error occurs in any processing and a screen for accepting an instruction of replacing the initial value with the changed value or canceling the change and leaving the initial value as it is. Even when there is an error, the combination "possible or impossible" determination processing of this embodiment permits the imaging, and thus the processing order of the common value determination processing, the slice matching determination processing and the OL amount determination processing is not considered.

Figure 5:
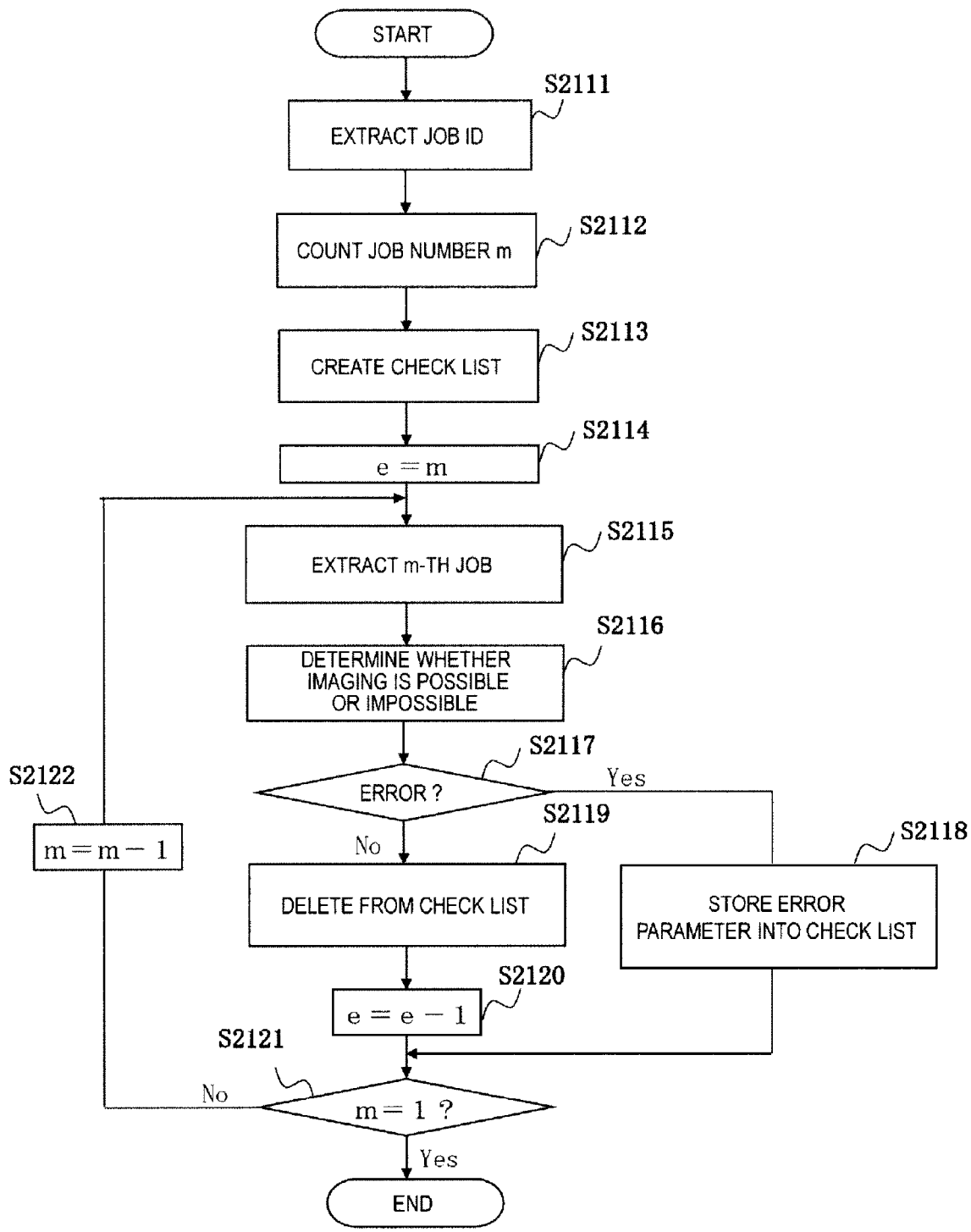
FIG. 5 is a processing flow of imaging "possible or impossible" PC processing according to the first embodiment.

The foregoing description relates to the summary of the parameter check processing of this embodiment. Next, the details of each processing will be described. First, the processing order of the imaging "possible or impossible" determination processing of this embodiment will be described. FIG. 5 shows imaging "possible or impossible" PC processing (step S211) of the imaging "possible or impossible" determining unit of this embodiment.

When accepting an instruction of the change, the imaging "possible or impossible" determining unit inquires to the sequence managing unit, and extracts the Job IDs 301 of a Job group containing the changed imaging parameter (step S2111). The number of Jobs for which the imaging parameter is changed is counted. In this case, it is represented by m (step S2112). The extracted Job ID and the imaging parameter (type and changed value) changed every Job are associated with each other in the decreasing order from m to 1 to create a check list (step S2113). In the subsequent processing, they are called as m-th, (m−1)-th, ..., first Job. Subsequently, the Job number m is stored in the error counter e (step S2114).

Thereafter, the imaging processing determining unit extracts an imaging sequence from the sequence managing table 300 and also extracts the permitted range of the changed imaging parameter from the parameter managing table with respect to the m-th Job of the check list (step S2115). Then, it is determined whether the changed value of the imaging parameter is within the corresponding permitted range or not (step S2116). When there is a changed value out of the permitted range, it is determined that there is an error, and when all the changed values are within the respective permitted ranges, it is determined that there is no error.

When there is an error (step S2117), an imaging parameter for which an error is determined is stored in the check list (step S2118), and the processing goes to step S2121. In this case, the imaging parameter of data as a determination target within the check list is replaced by only the error-determined imaging parameter, whereby the error-determined imaging parameter is stored in the check list. On the other hand, when there is no error (step S2117), the data of Job as a determination target is deleted from the check list (step S2119). Furthermore, when the error counter e is decremented by one (step S2120), and the processing goes to step S2121.

It is determined whether the imaging "possible or impossible" PC processing is executed on all Jobs for which imaging parameters are changed (m=1?) (step S2121). When the processing on all the jobs is finished, the processing is finished. On the other hand, there is non-processed Job, m is decremented by one (step S2122), and the processing returns to step S2115.

When the imaging "possible or impossible" PC processing is finished through the above processing, the imaging "possible or impossible" determining unit determines the presence or absence of an error in step S212. In this case, when the error counter e is equal to zero, it is determined that there is no error. When the error counter e is equal to one or more, it is determined that there is an error. It may be configured to determine without using the error counter e whether data remains in the check list. In this case, when data remains in the check list, it is determined that there is an error, and when no data remains, it is determined there is no error.

Figure 6:
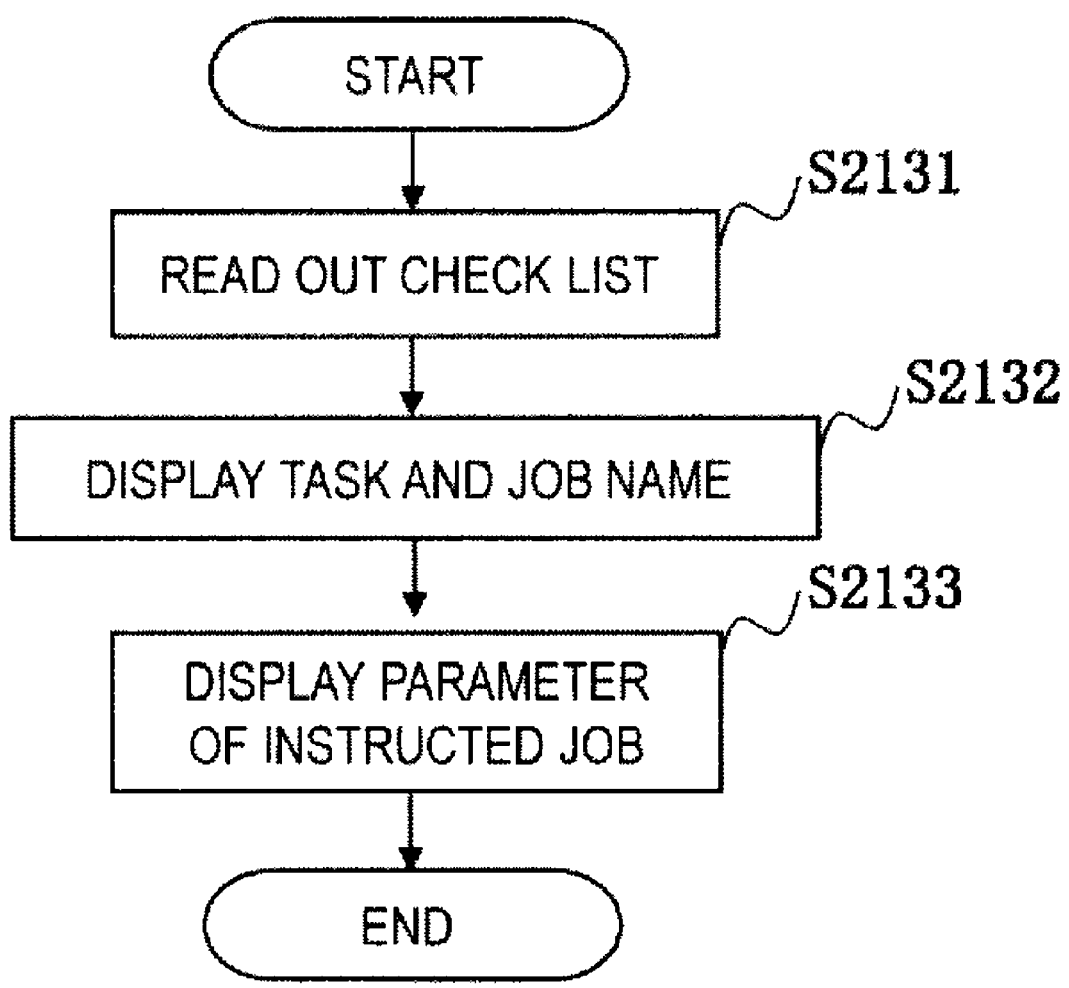
FIG. 6 is a processing flow of error display processing according to the first embodiment.

When it is determined in step S212 that there is an error, the processing goes to error display processing 213. FIG. 6 is a processing flow of the error display processing (step S213). The imaging "possible or impossible" determining unit reads out the check list (step S2131), and extracts Task name and Job name of each data on the list from the sequence managing table on the basis of Job ID to create an error display screen and display the error display screen on the display unit 115 (step S2132). Here, the error display screen of this embodiment has a first error display screen 500 for displaying Job in which an error occurs, and a second error display screen 510 for displaying an error-determined imaging parameter of each Job.

FIG. 7(a) shows an example of a first error display screen 700. As shown in FIG. 7(a), the first error display screen 700 has a Task name display area 701, a Job name display area 702 and a message display area 703, and a Job group in which the imaging parameter is determined as an error is displayed every Task. The Job name display area 702 also serves as an area for accepting an instruction for specifying Job displayed as a second error display screen. That is, the user specifies the Job name displayed in the Job name display area 702 by an operation such as clicking or the like, whereby Job to be displayed as the second error display screen 710 can be specified. In the first error display screen 700, the imaging sequence type used for Job may be displayed in addition to the Job name. It may be displayed in the message display area 703, for example, that the imaging parameter is out of the permitted range in the Job concerned and detailed information is obtained by clicking the Job name.

When an instruction for specifying Job is accepted from the user, the imaging "possible or impossible" determining unit reads out an error-determined imaging parameter of the Job concerned from the check list, and displays it on the second error display screen 710 (step S2133). FIG. 7(b) shows an example of the second error display screen 710. The second error display screen 710 has an area 711 for displaying information (Task name and Job name) for specifying Job, an area 712 for displaying the type of an error-determined imaging parameter, and a cancel button 713 for accepting an instruction of returning to the first error display screen 700. The user can know the error-determined imaging parameter on the basis of the above display, and determine the subsequent processing.

Next, the detailed processing procedure of the common value determination processing (step S221), the slice matching determination processing (step S222) and the OL amount determination processing (step S223) in the combination "possible or impossible" determination processing (step S220) of this embodiment will be described. The following description will be made on the assumption that the common value determination processing, the slice matching determination processing and the OL amount determination processing are successively executed in this order.

Figure 8:
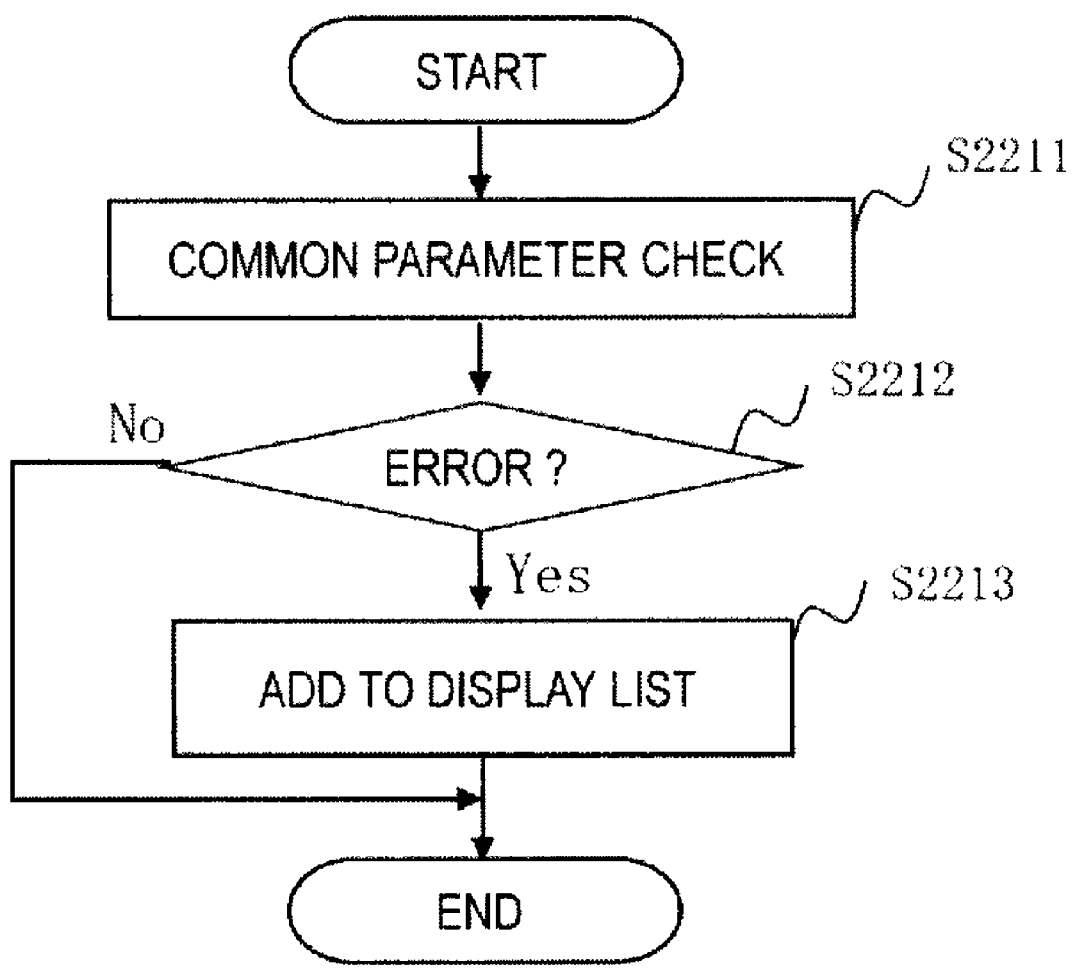
FIG. 8 is a processing flow of common value determination processing of the first embodiment.

When receiving a notification of the end of the processing from the imaging "possible or impossible" determining unit, the combination "possible or impossible" determining unit executes the common value determination processing of checking whether the imaging parameters to be the same value among plural Jobs are set to the same value in the changed value set. FIG. 8 is a processing flow of the common value determination processing (step S221) of the combination processing determining unit of this embodiment. In this embodiment, the imaging parameters (common parameter) which should have the same value among Jobs in one Task, Jobs in one group, all Jobs in all Tasks are extracted, and it is checked whether these parameters are equal to the same value (step S2211). For example, the imaging parameter types which should have the same values among Jobs in one Task are FOV, rectangle rate, phase encode direction, bed position, reception coil, reception coil mode, etc. Furthermore, imaging parameters which should have the same values among Jobs in one group are slice face (imaging step plane), oblique angle, etc. The imaging parameter types which should have the same values are stored in the storage unit 116 in advance.

Subsequently, when there are non-identical values in these imaging parameter types, it is determined that there is an error (step S2212). At this time, an error-determined imaging parameter and Job ID of a Job group in a range in which the imaging parameter concerned should have the same value are recorded in a common value error display list (step S2213). On the other hand, when there is no error, the processing is finished, and the processing is shifted to the slice matching determination processing (step S222).

Figure 9:
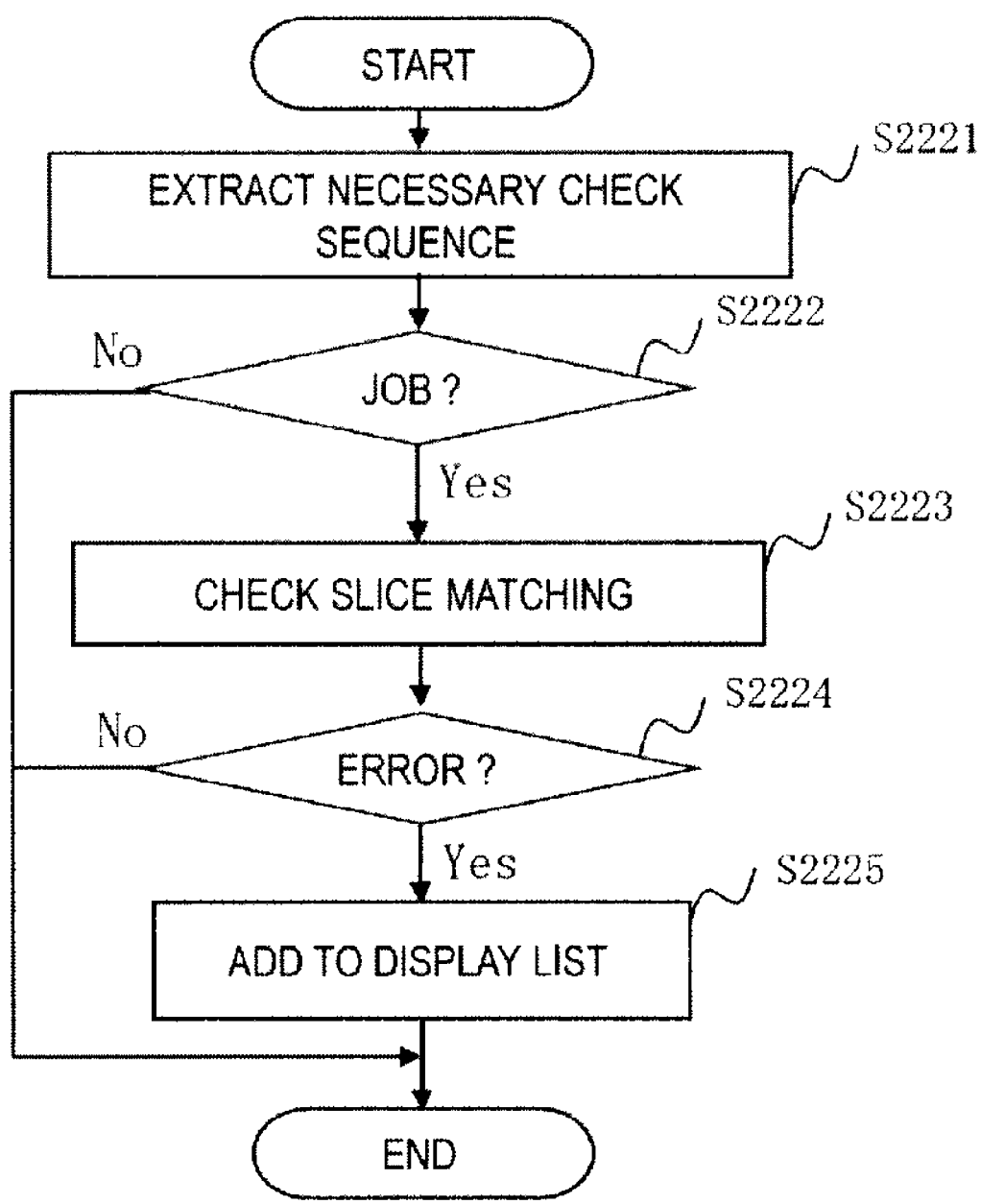
FIG. 9 is a processing flow of a slice matching determination processing of the first embodiment.

FIG. 9 is a processing flow of the slice matching determination processing (step S222). In the slice matching determination processing (S222), the combination "possible or impossible" determining unit first determines whether an imaging sequence for which slice matching should be determined is contained or not (step S2221). For example, when each Job is associated with only imaging targeting an axial plane, the slice matching processing is unnecessary. In this case, the processing is finished. The condition of necessity or not is stored in the storage unit 116 in advance.

When a necessary Job is contained, the slice matching is checked (step S2222). In this case, the matching between the interval of slices and the number of slices (or slice thickness) in the imaging parameters is checked between Jobs in each group in the changed value set. That is, it is determined whether the difference between them is within a permitted range although both are identical or different (step S2224). When the condition described above is satisfied, matching is determined, no error is determined and the processing shifts to the OL amount determination processing (step S223). On the other hand, when mismatching is determined, it is determined that there is an error, Job ID belonging to a mismatched group is added to a slice matching error display list (step S2225), and then the processing shifts to the OL amount determination processing (step S223).

Figure 10:
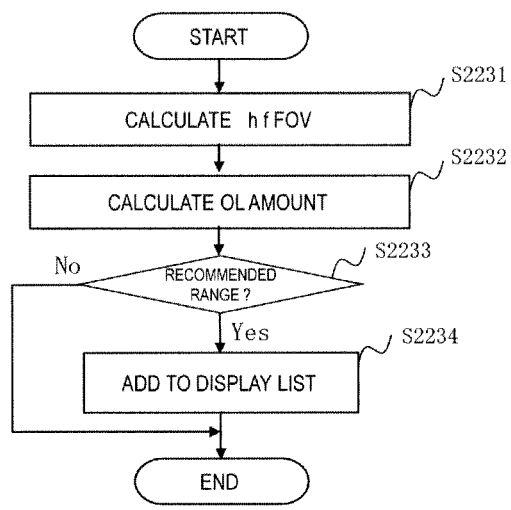
FIG. 10 is a processing flow of OL amount determination processing of the first embodiment.

FIG. 10 is a processing flow of the OL amount determination processing (step S223). In the OL amount determination processing (step S223), the combination "possible or impossible" determining unit determines every group whether the OL amount of the reconstructed images of adjacent stations is a combinable range or not. The detailed procedure of the determination will be described below.

First, an imaging area size hfFOV of each station (the imaging area in the body axial direction of the station) is calculated by using the changed value set (step S2231). With respect to hfFOV, the calculation thereof is different in accordance with the imaging cross-section. When the imaging cross-section is a coronal cross-section or sagittal cross-section, it can be calculated by a different mathematical expression in accordance with the phase encode direction. When the phase encode direction is the body axial direction, hfFOV is calculated by the following mathematical expression (1).

$$hfFOV = FOV \times \text{rectangle rate} \tag{1}$$

When the phase encode direction is vertical to the body axis, hfFOV is calculated by the following mathematical expression (2).

$$hfFOV = FOV \tag{2}$$

Furthermore, when the imaging cross-section is an axial cross-section, hfFOV is calculated by the following mathematical expression (3).

$$hfFOV = (\text{number of slices} - 1) \times \text{slice interval} + \text{slice thickness} \tag{3}$$

Figure 11:
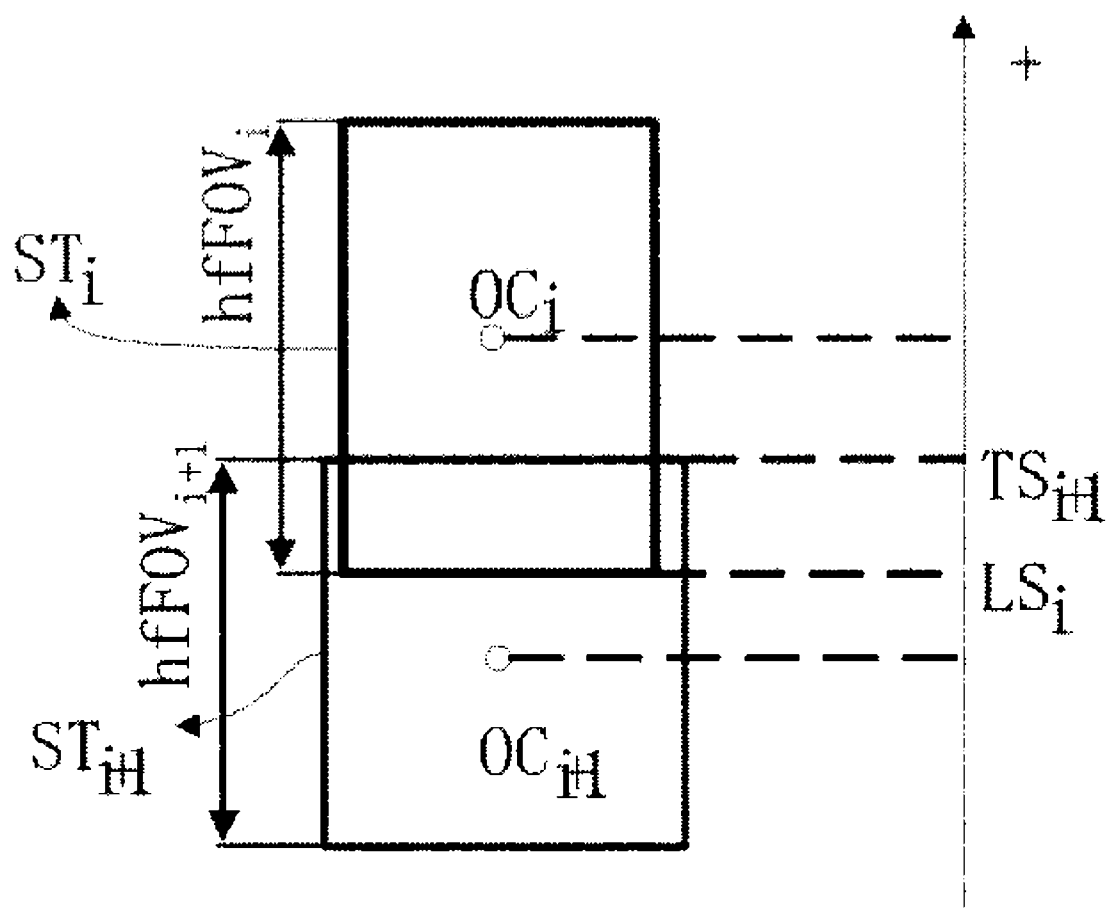
FIG. 11 is a diagram showing OL amount calculation of the first embodiment.

Then, the OL amount between the adjacent stations is calculated by using the calculated hfFOV (step S2232). FIG. 11 is a diagram showing the OL amount calculation between the adjacent stations. The OL amount is calculated from hfFOV and the station position. The station position is the bed position of each station (a sign-affixed coordinate representing the center of FOV in the body axial direction). The bed position is one of the imaging parameters as described above.

The station position (bed position) is hereinafter referred to as OC. When the adjacent two stations are represented by $ST_i$, $ST_{i+1}$, and hfFOV and OC of the respective stations $ST_i$, $ST_{i+1}$ are represented by $hfFOV_i$, $hfFOV_{i+1}$, $OC_i$–$OC_{i+1}$, OL is calculated by the following mathematical expression (4). $OC_i$, $OC_{i+1}$ are sign-affixed values.

$$OL = (hfFOV_i + hfFOV_{i+1})/2 + OC_i - OC_{i+1} \tag{4}$$

Subsequently, it is determined whether the calculated OL amount is within a recommended range of OL (from $dOL_{Min}$ to $dOL_{Max}$) (step S2233). Here, with respect to the recommended range from $dOL_{Min}$ to $dOL_{Max}$, the minimum OL amount $dOL_{Min}$ and the maximum OL amount $dOL_{Max}$ are determined in consideration of the image quality of the combined image and the examination time. $dOL_{Min}$ represents the minimum OL amount indispensable to insure a fixed image quality and $dOL_{Max}$ is an OL amount at which further increase of the OL amount increases a demerit that the examination time is long as compared with a merit that the image quality is enhanced. $dOL_{Min}$ to $dOL_{Max}$ are predetermined and stored in the storage unit 116.

With respect to all the groups, when the OL amount between adjacent stations is within the recommended range, the OL amount is determined to be proper, and the OL amount determination processing is finished. On the other hand, when the OL amount is out of the recommended range, JOB IDs of adjacent Jobs in the group concerned are added to the OL amount error display list (step S2234), and the OL amount determination processing is finished.

As described above, according to this embodiment, when the user changes the imaging parameter in the multistation/multisequence imaging, the parameter check processing described above is executed, and it is determined in a lump before the start of the imaging whether the changed imaging parameter is proper or not. The "proper or not" determination is first performed from the viewpoint of the "possible or impossible" determination of the imaging, and when it is determined that the imaging is possible, it is subsequently determined from the viewpoint of the "possible or impossible" determination of the combination.

In this embodiment, when it is determined in the "possible or impossible" determination of imaging that the imaging is improper, the imaging is not permitted, and the Job and the imaging parameter thereof are presented to the user. Accordingly, the user can watch the display to recognize the improper imaging parameter, and change the value of the imaging parameter again. As described above, according to this embodiment, in the multistation/multisequence imaging for executing many imaging sequences, when imaging parameters are changed, possibility or impossibility of the change of the imaging parameters are determined in a lump before the imaging is started. Accordingly, it can be easily determined whether the imaging after imaging parameters are changed can be performed or not. Furthermore, the imaging is not executed until imaging parameters which enable the imaging are set, and thus needless imaging which brings an error is not executed.

Furthermore, according to this embodiment, there is no waste because the "possible or impossible" determination of the imaging and "possible or impossible" determination of the combination can be performed separately from each other, and the "possible or impossible" determination of the combination is executed only when the imaging is determined to be possible.

This embodiment is configured so that the parameter check processing described above is executed in the signal processor 107 in the MRI apparatus 100. However, this embodiment is not limited to this configuration. For example, the parameter check processing of this embodiment may be executed in an information processing device which is independent of the MRI apparatus 100 and can transmit/receive data to/from the MRI apparatus 100. At this time, various kinds of data necessary for the parameter check processing may be stored in the storage unit 116 of the MRI apparatus 100 as in the case of the above embodiment, and may be stored in a storage device equipped to the information processing device.

Furthermore, a construction of accepting an instruction of further changing each error-determined imaging parameter simultaneously with the display of the imaging parameter concerned, an instruction of returning all imaging parameters of displayed Job to values before the change, etc. may be displayed on the second error display screen 710. Furthermore, a construction of accepting an instruction of returning imaging parameters of all Jobs containing error-determined imaging parameters to values before the change and/or an instruction of returning the imaging parameters of all the Jobs to values before the change may be displayed on the first error display screen 700.

Second Embodiment

Next, a second embodiment to which the present invention is applied will be described. The MRI apparatus of this embodiment is basically the same as the first embodiment. In the first embodiment, when there is an error, the imaging "possible or impossible" determining unit in the parameter check unit displays the fact that there is an error, thereby promoting the user to change. However, in this embodiment, the value of a recommended imaging parameter is presented as a suggestion to the user so that the suggestion can be selected. The construction of this embodiment which is different from the first embodiment will be mainly described hereunder.

Figure 12:
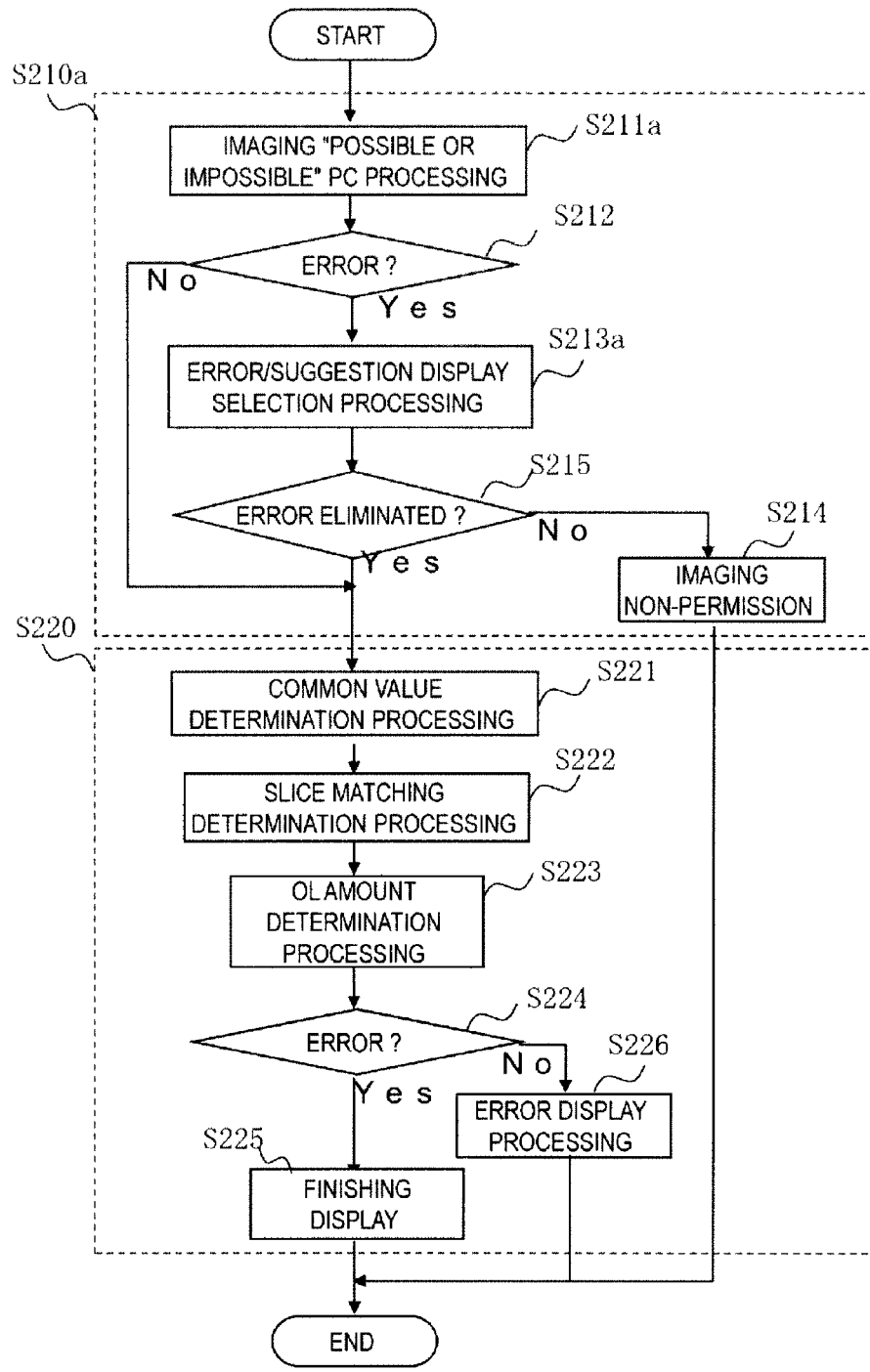
FIG. 12 is a processing flow of parameter check processing according to a second embodiment.

FIG. 12 is a processing flow of the parameter check processing according to the embodiment. In this case, it is also assumed that the processing is started when an input of changing an imaging parameter is accepted from the user. The steps of the same processing as the first embodiment are represented by the same reference numerals.

When the instruction of changing the imaging parameter is accepted through the input unit 114, the imaging "possible or impossible" determining unit executes the imaging "possible or impossible" determination processing of determining whether the imaging is possible or impossible by the accepted changed value (step S210a). In this case, when accepting the instruction of the change, the imaging "possible or impossible" determining unit inquires to the sequence managing unit, extracts the Job group in which the imaging parameter is changed, and executes on each JOb the imaging "possible or impossible" parameter check (PC) processing of determining whether the imaging is possible or impossible (step S211a). In the imaging "possible or impossible" PC processing of this embodiment, it is determined whether the changed value is within a predetermined range or not. When there is an imaging parameter whose changed value is out of the range, the imaging parameter is determined as an error, and a suggestion is calculated as a recommended value.

When there is an error (step S212), the imaging "possible or impossible" determining unit executes error/suggestion display selection processing for displaying a suggestion and an error (step S213a), and then accepts selection of a suggestion or the like from the user through the input unit 114. With respect to all the error-determined imaging parameters, it is determined whether the change to the suggestion or the like is accepted or not, that is, whether errors are eliminated or not (step S215). When all the errors are eliminated, the imaging "possible or impossible" determination processing is finished, and then the processing shifts to the combination "possible or impossible" determination processing. The combination "possible or impossible" determination processing after the shift is the same as the first embodiment.

On the other hand, there is some error-determined imaging parameter which does not accept selection of a suggestion or the like, the imaging is not permitted, this fact is displayed (step S214), and the parameter check processing is finished.

The processing different from the first embodiment will be described hereunder. The details of the imaging "possible or impossible" PC processing (step S211a) and error suggestion display selection processing (step S213a) will be described.

Figure 13:
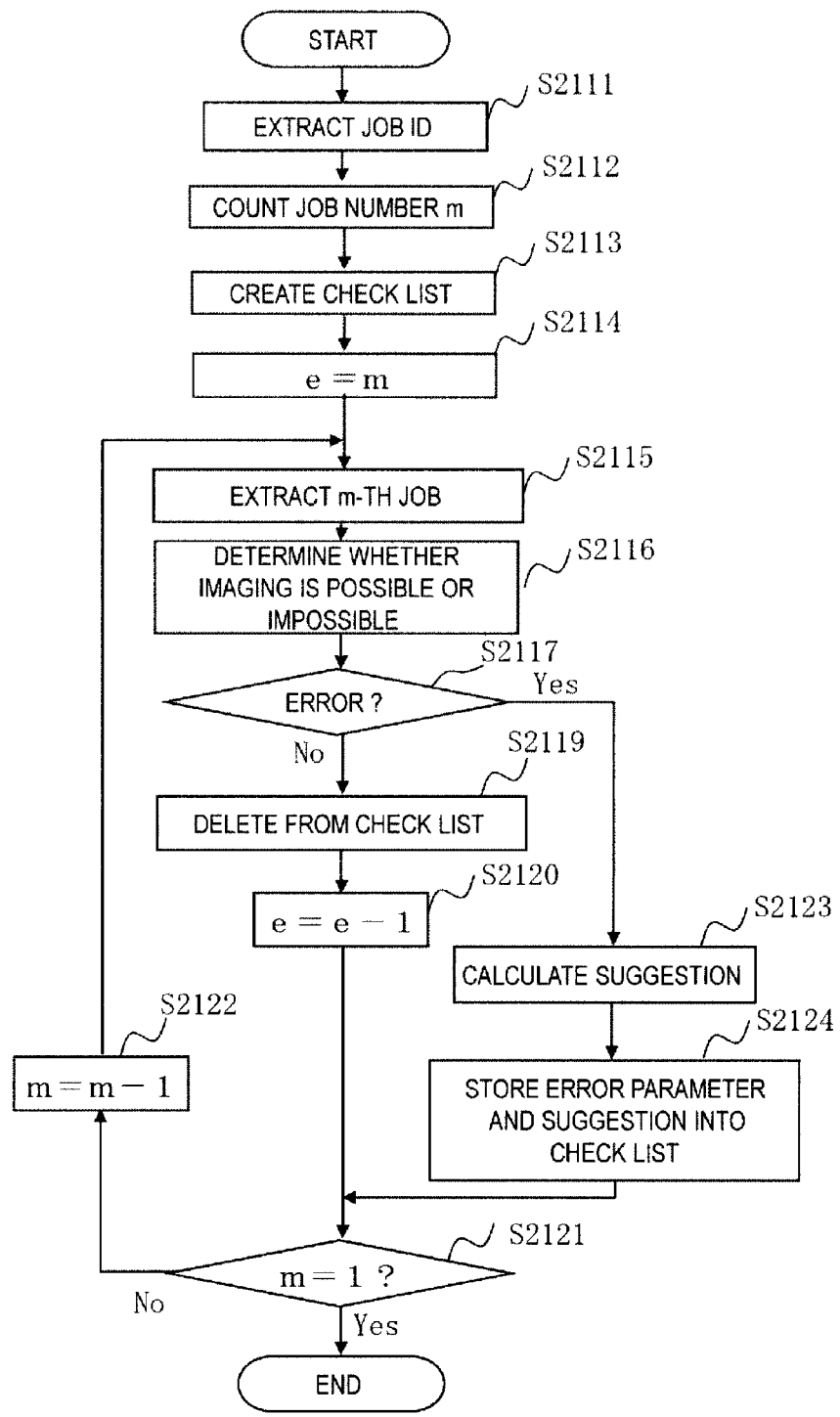
FIG. 13 is a processing flow of imaging "possible or impossible" PC processing of the second embodiment.

FIG. 13 is a processing flow of the imaging "possible or impossible" PC processing of this embodiment. This embodiment is basically the same as the imaging "possible or impossible" PC processing of the first embodiment. However, this embodiment is provided with suggestion calculation processing for calculating a suggestion as a recommended value when the changed imaging parameter is out of the permitted range (step S2123). Furthermore, the suggestion is stored in the check list in association with the error-determined imaging parameter (step S2124). In the suggestion calculation processing, the imaging "possible or impossible" determining unit calculates as a suggestion a value which is within the permitted range of the imaging parameter and nearest to the changed value input by the user. The other processing is identical to the processing of the same reference numerals of the first embodiment.

Figure 14:
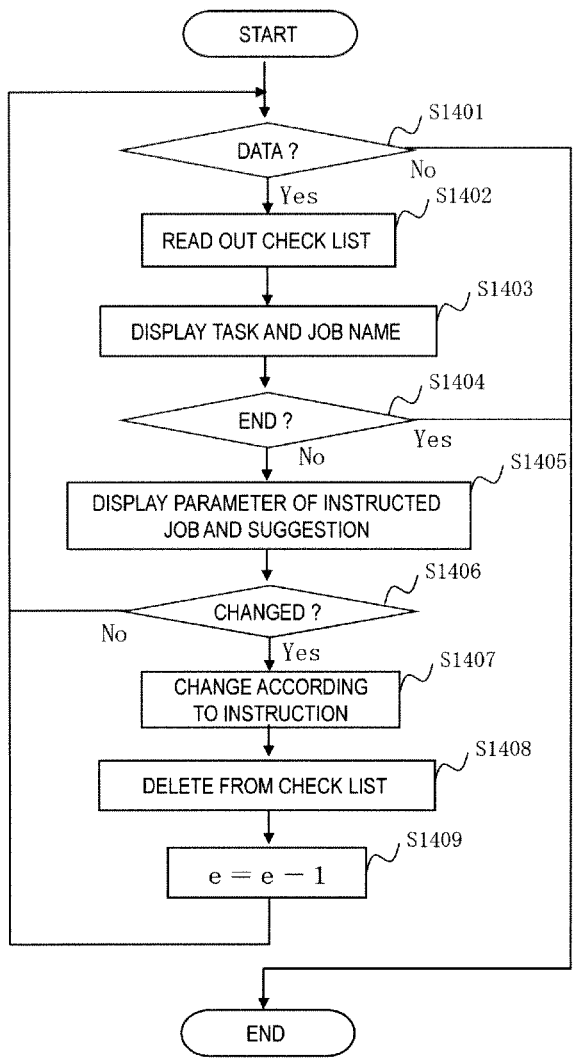
FIG. 14 is a processing flow of an error suggestion display selection processing of the second embodiment.

Next, the details of the error/suggestion display selection processing (step S213a) will be described. FIG. 14 is a processing flow of the error/suggestion display selection processing of this embodiment.

In the error/suggestion display selection processing, the imaging "possible or impossible" determining unit first checks the presence or absence of data in the check list (step S1401). This is because when an imaging parameter is changed to a recommended value or the like displayed as a suggestion, data is deleted from the check list in this embodiment. When there is no data, the error/suggestion display selection processing is finished.

When there is data, the imaging "possible or impossible" determining unit reads out the check list (step S1402), Task name and Job name of each data on the list are extracted from the sequence managing table on the basis of Job ID, and a first error/suggestion display screen 1500 is generated, and displayed on the display unit 115 (step S1403). FIG. 15(a) shows an example of the displayed first screen error/suggestion display screen 1500. The first screen error/suggestion display screen 1500 is basically the same as the first error display screen 700 of the first embodiment, and has a Task name display area 1501, a Job name display area 1502 and a message display area 1503. The first error/suggestion display screen 1500 of this embodiment is further provided with a finishing button 1504 for accepting a finishing instruction.

When push of the finishing button 1504 is accepted (step S1404), the imaging "possible or impossible" determining unit finishes the error/suggestion display selection processing. On the other hand, when an instruction of specifying Job is accepted from the user (step S1404), the type of an error-determined imaging parameter of the Job concerned is read out from the check list and displayed (step S1405). At this time, in this embodiment, the suggestion is further read out and displayed. FIG. 15(*b*) shows an example of a second screen error/suggestion display screen 1510 displayed at this time. As shown in FIG. 15(*b*), the second error/suggestion display screen 1510 of this embodiment has an area 1511 in which information for specifying Job is displayed, an area 1512 in which an error-determined imaging parameter is displayed, an area 1513 in which a suggestion for each imaging parameter is displayed, a change instruction accepting area 1514 for accepting an instruction of changing to a recommended value displayed as a suggestion or returning to a value before change (initial value), and a settling instruction accepting area 1515 for accepting an instruction of settling the selection. In the settling instruction accepting area 1515 are displayed an OK button for accepting an instruction of changing to a value instructed through the change instruction accepting area 1514, and a cancel button for accepting an instruction of returning to the first error/suggestion display screen.

The user can know an error-determined imaging parameter and a suggestion as a recommended value for the imaging parameter concerned by watching the display of the second error/suggestion display screen 1510. Furthermore, by making an instruction through the change instruction accepting area 1514, an instruction of changing to the suggestion or returning to the value before the change can be made every imaging parameter. The imaging "possible or impossible" determining unit accepts an instruction of changing or returning to the first error/suggestion display screen 1500 through the settling instruction accepting display area 1515.

When the imaging "possible or impossible" determining unit accepts an instruction of changing to the recommended value or the initial value with respect to the displayed Job (step S1406), the imaging "possible or impossible" determining unit changes the changed value of the imaging parameter of the Job concerned according to each instruction (step S1407), and deletes the Job concerned from the check list (step S1408). Furthermore, the error counter e is decremented by one (step S1409), and then the processing returns to the step S1401.

In the imaging "possible or impossible" determination processing (step S210*a*) of this embodiment, the determination as to whether the error is eliminated or not (step S215) is executed on the basis of the presence or absence of data in the check list or the value of the error counter e. That is, when the check list contains no data or when the value of the error counter e is equal to zero, it is determined that the error is eliminated. In the other cases, it is determined that the error is not eliminated.

As described above, according to this embodiment, the user can obtain a recommended value within the permitted ranged with respect to an error-determined imaging parameter. By selecting this recommended value, the imaging parameter can be easily set to a value in the permitted range. Accordingly, in addition to the effect obtained in the first embodiment, even when the imaging parameter is changed, an imaging parameter which can surely perform the imaging can be easily set.

In this embodiment, a construction of accepting an instruction of further changing each error-determined imaging parameter may be displayed on the second error/suggestion display screen 1510 as in the case of the first embodiment. Furthermore, a construction of instructing all error-determined imaging parameters to values before the change and/or an instruction of returning all the imaging parameters to the values before the change may be displayed on the first error display screen 1500.

Furthermore, in this embodiment, a suggestion of Job instructed by the user is displayed with respect to an error-determined imaging parameter, however, this embodiment is not limited to this. For example, in the error/suggestion display selection processing, all imaging parameters which are read out from the check list and determined as errors may be displayed together with suggestions every Task and Job. In this case, the processing of displaying all the error-determined imaging parameters together with the suggestions may be executed in place of the step of displaying Job using an error-determined parameter (step S1403) and the step of displaying an error-determined imaging parameter of an instructed Job (step S1405).

Furthermore, the error/suggestion display processing is not executed after the advisability of the imaging parameter is checked with respect to all the Jobs, but the above embodiment may be configured in the imaging "possible or impossible" PC processing so that a suggestion is displayed simultaneously with storage of the suggestion concerned into the check list when the suggestion is calculated (step S2123), thereby requesting user's instruction.

Third Embodiment

Next, a third embodiment of the present invention will be described. An MRI apparatus of this embodiment is basically the same as the second embodiment. However, in this embodiment, when there is an error in the imaging parameter, it is automatically replaced by the suggestion calculated as a recommended value. A construction of this embodiment which is different from the second embodiment will be mainly described hereunder.

Figure 16:
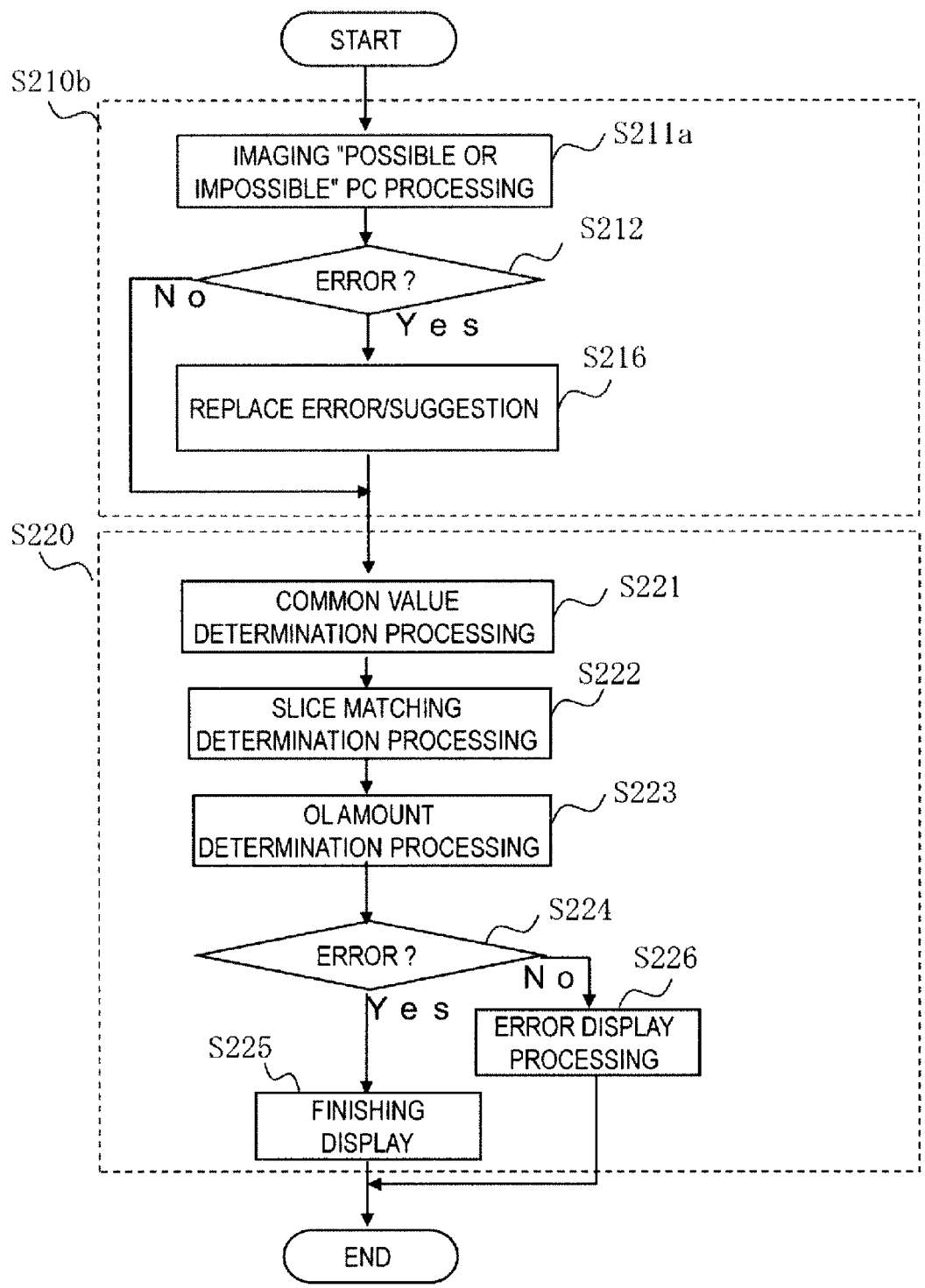
FIG. 16 is a processing flow of parameter check processing according to a third embodiment.

FIG. 16 shows a processing flow of the parameter check processing of this embodiment. Here, it is assumed that the processing is started when an input of the change of an imaging parameter is accepted from a user. The same processing as the second embodiment is represented by the same reference numeral.

When the change of an imaging parameter is accepted through the input unit 114, the imaging "possible or impossible" determining unit executes the imaging "possible or impossible" determination processing of determining whether the imaging is possible by an accepted changed value (step S210*b*). In this case, when accepting an instruction of the change, the imaging "possible or impossible" determining unit inquires to the sequence managing unit, extracts a Job group in which the imaging parameter is changed, and executes the imaging "possible or impossible" parameter check (PC) processing of determining whether the imaging is possible or impossible with respect to each Job (step S211*a*).

In the imaging "possible or impossible" PC processing of this embodiment, it is determined whether the changed value is within a predetermined range or not. When there is an imaging parameter whose changed value is out of the range, the imaging parameter is determined as an error, and also a suggestion is calculated as a recommended value.

When there is an error (step S212), the imaging "possible or impossible" determining unit executes the error/suggestion replacing processing of replacing the changed value of the error-determined imaging parameter by the recommended value calculated as the suggestion (step S216), finishes the imaging "possible or impossible" determining processing and then shifts to the combination "possible or impossible" determination processing. When there is no error in step S212, the imaging "possible or impossible" determination processing is finished, and the processing shifts to the combination "possible or impossible" determination processing. The combination "possible or impossible" determination processing after the shift (step S220) is the same as the first and second embodiments.

As described above, according to this embodiment, in a case where an imaging parameter is changed in the multistation/multisequence imaging, even when a value out of the permitted range is input, the value concerned is changed to a value within the permitted range before imaging is started. Accordingly, an imaging parameter with which imaging can be certainly performed is set, and thus imaging never fails.

In this embodiment, when there is an error-determined imaging parameter in the imaging "possible or impossible" PC processing before the imaging "possible or impossible" determination processing is started, the changed value may be selectively replaced by a suggestion value or an initial value.

Fourth Embodiment

Next, a fourth embodiment to which the present invention is applied will be described. An MRI apparatus according to this embodiment is basically the same as any one of the first to third embodiments, however, the combination "possible or impossible" determination processing of the combination "possible or impossible" determining unit is different. The combination "possible or impossible" determination processing of this embodiment which is different from that of each of the first to third embodiments will be described hereunder.

As in the case of the first to third embodiments, the combination "possible or impossible" determining unit executes the common value determination processing, the slice matching determination processing and the OL amount determination processing. However, unlike each of the embodiments, these processing is certainly executed in this order in this embodiment, the error display processing is executed every processing and it is inquired to a user whether the processing proceeds. The combination "possible or impossible" determination processing of the combination "possible or impossible" determining unit according to this embodiment will be described hereunder.

Figure 17:
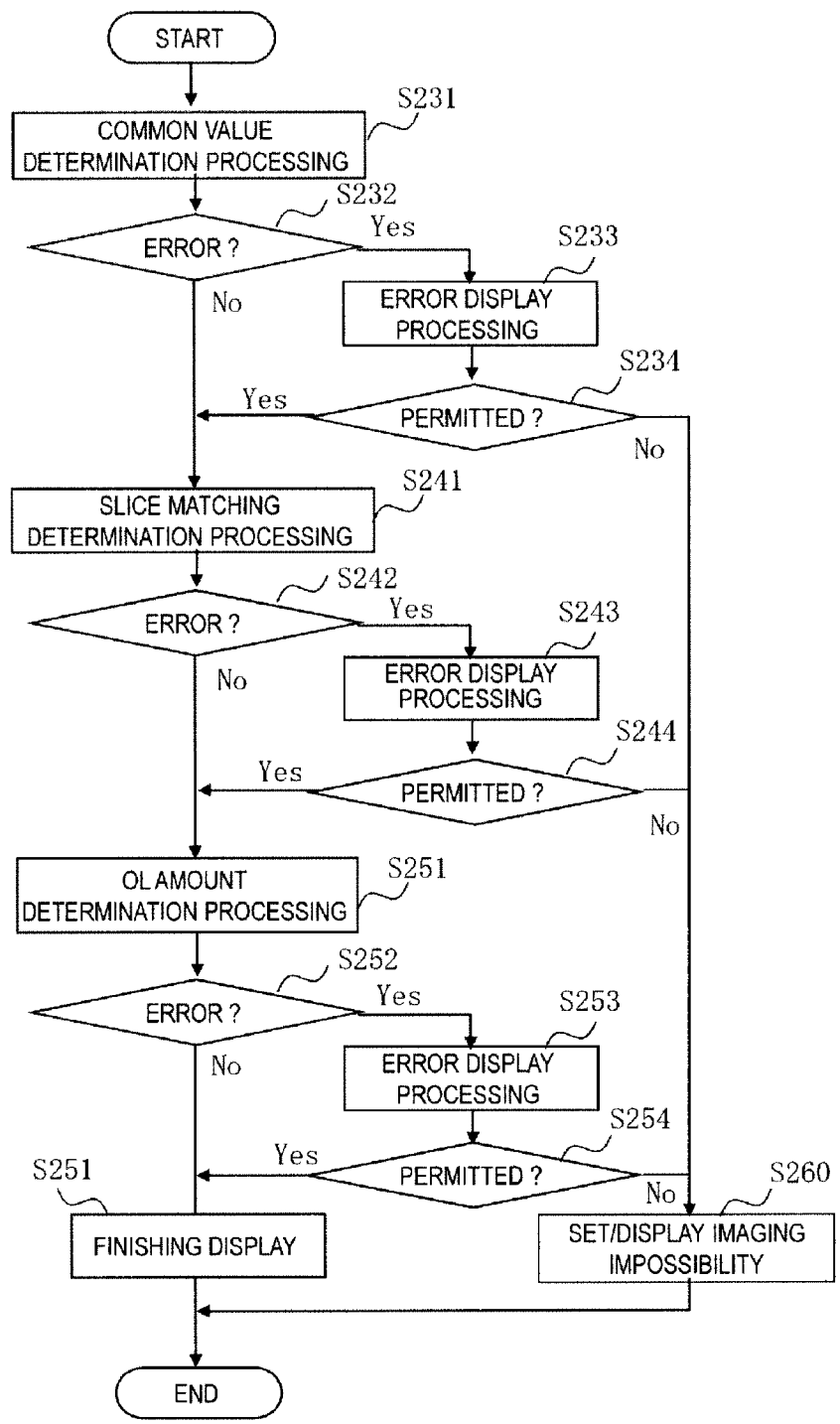
FIG. 17 is a processing flow of combination "possible or impossible" determination processing according to a fourth embodiment.

FIG. 17 is a processing flow of the combination "possible or impossible" determination processing of this embodiment. In this embodiment, the combination "possible or impossible" determining unit executes the common value determination processing (step S231). The details of this processing are the same as the common value determination processing of each of the embodiments described above, and the presence or absence of an error is determined (step S232). When it is determined that there is an error, the error display processing is executed (step S233). In this case, information recorded in a common value error display list and a button for accepting from a user an intention as to whether the imaging based on an error-occurring imaging parameter is permitted or not are displayed as a common value error display screen.

Figure 18:
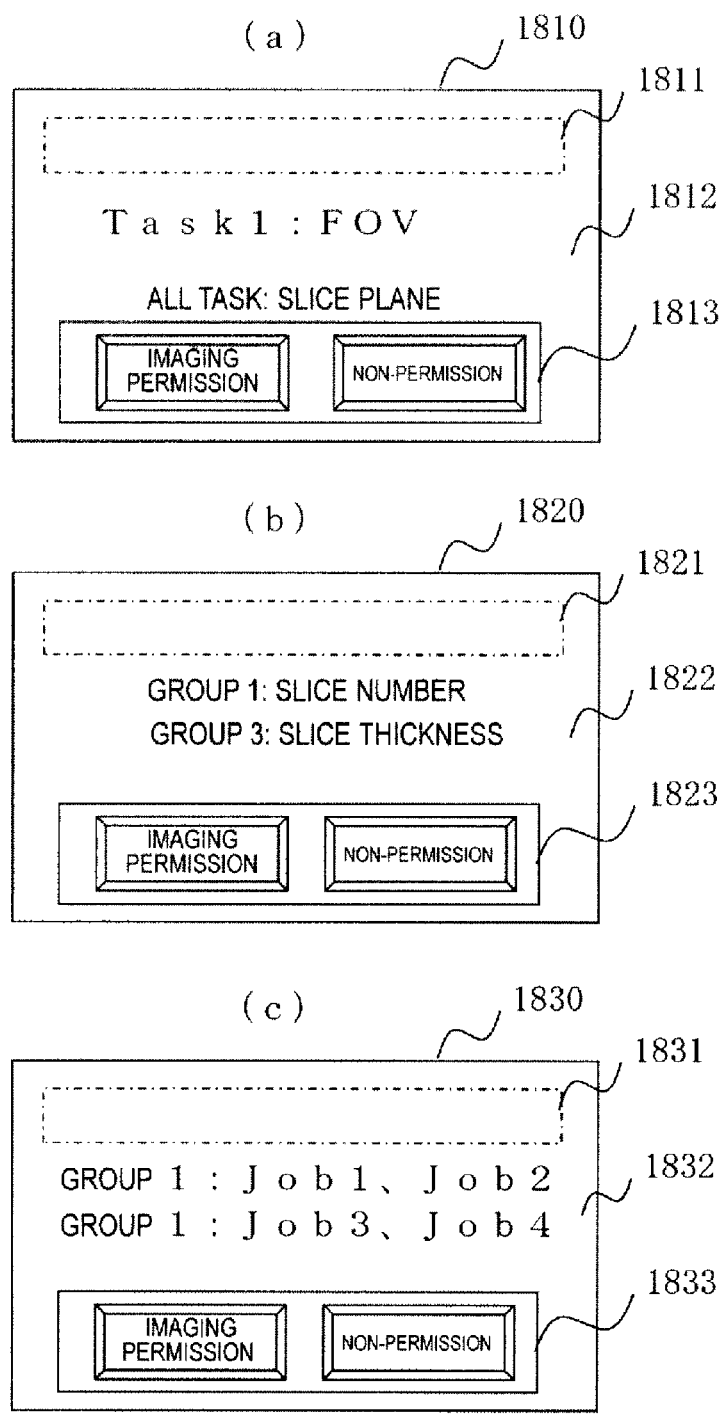
FIG. 18 shows an example of an error display screen of the fourth embodiment.

FIG. 18(a) shows an example of a common value error display screen 1810. As shown in FIG. 18(a), the common value error display screen 1810 of this embodiment has a message display unit 1811, an error information display unit 1812 for displaying information for specifying an error-occurring Job group and an imaging parameter, and a button unit 1813 for accepting an intention as to whether imaging is possible or not. When a permission instruction is accepted through the button unit 1813 (step S234), the processing is continued, and shifts to step S241. On the other hand, when an intention of non-permission is accepted (step S234), the processing goes to step S260 to set the imaging to impossibility, and the combination "possible or impossible" determination processing is finished.

Subsequently, the combination "possible or impossible" determining unit executes the slice matching determination processing (step S241). The details of this processing are the same as the slice matching determination processing of each of the above embodiments, and the presence or absence of an error is determined (step S242). When it is determined that there is an error, the error display processing is executed (step S243). In this case, information recorded in the slice matching error display list and a button for accepting an user's intention as to whether imaging based on an error-occurring imaging parameter is permitted or not are displayed as the slice matching error display screen.

FIG. 18(b) shows an example of the slice matching error display screen 1820. As shown in FIG. 18(b), the slice matching error display screen of this embodiment has a message display unit 1821, an error information display unit 1822 for displaying information for specifying an error-occurring group and an imaging parameter, and a button unit 1823 for accepting an intention as to whether imaging is possible or impossible. When a permitting instruction is accepted through the button unit 1823 (step S244), the processing is continued and the processing shifts to step S251. On the other hand, when an intention of non-permission is accepted (step S244), the processing goes to step S260 to set that the imaging is impossible, and the combination "possible or impossible" determination processing is finished.

Subsequently, the combination "possible or impossible" determining unit executes the OL amount determination processing (step S251). The details of this processing are the same as the OL amount determination processing of each of the above embodiments. Then, the presence or absence of an error is determined (step S252). When it is determined that there is an error, the error display processing is executed (step S253). In this case, information recorded in the OL amount error display list and a button for accepting an user's intention as to whether the imaging based on an error-occurring imaging parameter is permitted or not are displayed as the OL amount error display screen.

FIG. 18(c) shows an example of an OL amount error display screen 1830. As shown in FIG. 18(c), the OL amount error display screen 1830 of this embodiment has a message display unit 1831, an error information display unit 1832 for displaying information for specifying an error-occurring group and a button unit 1833 for accepting an intention as to whether imaging is possible or not. When a permitting instruction is accepted through the button unit 1833 (step S254), a finishing display is made (step S261), and the processing is finished. A screen for accepting a final instruction of replacing the initial value with the changed value is displayed in the finishing display as in the case of each of the above embodiments.

On the other hand, when an intention of non-permission is accepted (step S234), the processing goes to step S260 to set that the imaging is impossible and displays this fact (step S260), and then the combination "possible or impossible" determination processing is finished.

When the imaging is set to be impossible, a display for allowing the imaging parameter to be changeable again may be made. When the imaging parameter is changed, the imaging "possible or impossible" determination processing is executed.

Furthermore, in this embodiment, when there is an error in each processing, it is inquired to the user whether imaging is possible or impossible. However, this embodiment is not limited to this style. For example, the next slice matching determination processing may be executed only when there is no error in the common value determination processing, the next OL amount determination processing may be executed only when there is no error in the slice matching determination processing, and the imaging may be set to be impossible without inquiring about whether the imaging is possible or impossible when there is an error in each processing.

In this case, FOV is unified among Jobs in each Task by the common value determination processing described above, and thus the slice matching determination processing and the OL amount determination processing may be executed, not among Jobs in a group, but on a Task basis. The Task-basis execution can increase the processing speed.

Furthermore, in each processing, the recommended value may be displayed in the error display processing (step S233, S243, S253). The recommended value is calculated when an error is determined in each processing. For example, in the common value determination processing, a value having the largest number at the processing time point in a group of Jobs which should have the same value is set as a recommended value. Furthermore, in the slice matching determination processing, a value having the largest number at the processing time point in a group of Jobs which should be coincident is set as a recommended value. In the OL amount determination processing, a value nearest to the value of an error-occurring imaging parameter within an OL amount recommended range is set as a recommended value.

As described above, according to this embodiment, when it is determined that the combination is impossible, the imaging can be determined to be impossible, and thus a composite image having high image quality can be surely obtained. Accordingly, the quality of the composite image can be enhanced in addition to the effect obtained in each of the above embodiments. Furthermore, when an error occurs in the determination processing described above at the step of determining whether the combination is possible or impossible, the imaging is determined to be impossible, and the processing can be finished without executing the following determination processing. Therefore, it is unnecessary to execute needless processing. Accordingly, the processing efficiency can be enhanced.

Furthermore, according to each of the above embodiments, in the multistation/multisequence imaging in which imaging is performed while an examinee is divided into plural stations as in the case of whole body MRI, the imaging can be prevented from stopping at some midpoint of the imaging process due to defect of an imaging parameter. Therefore, the examination time can be shortened, and the usability can be enhanced because the operation is simple.

In the above embodiments, the description is made by exemplifying the multistation/multisequence imaging. However, the method of each of the above embodiment can be directly applied to even multistation/single-sequence imaging.

Furthermore, in each of the above embodiments, the change of the imaging parameter is described to have an effect on only the corresponding Job. However, this invention is not limited to this assumption. For example, the embodiments may be configured so that a Job group in which it is determined that the same imaging parameter is used in the same imaging sequence is specified, and when an imaging parameter is changed in one Job of the Job group, all the same imaging parameters in the Job group concerned are changed. In this case, information for associating relevant Job groups (link information) is stored in the storage unit 116 in advance.

Figure 19:
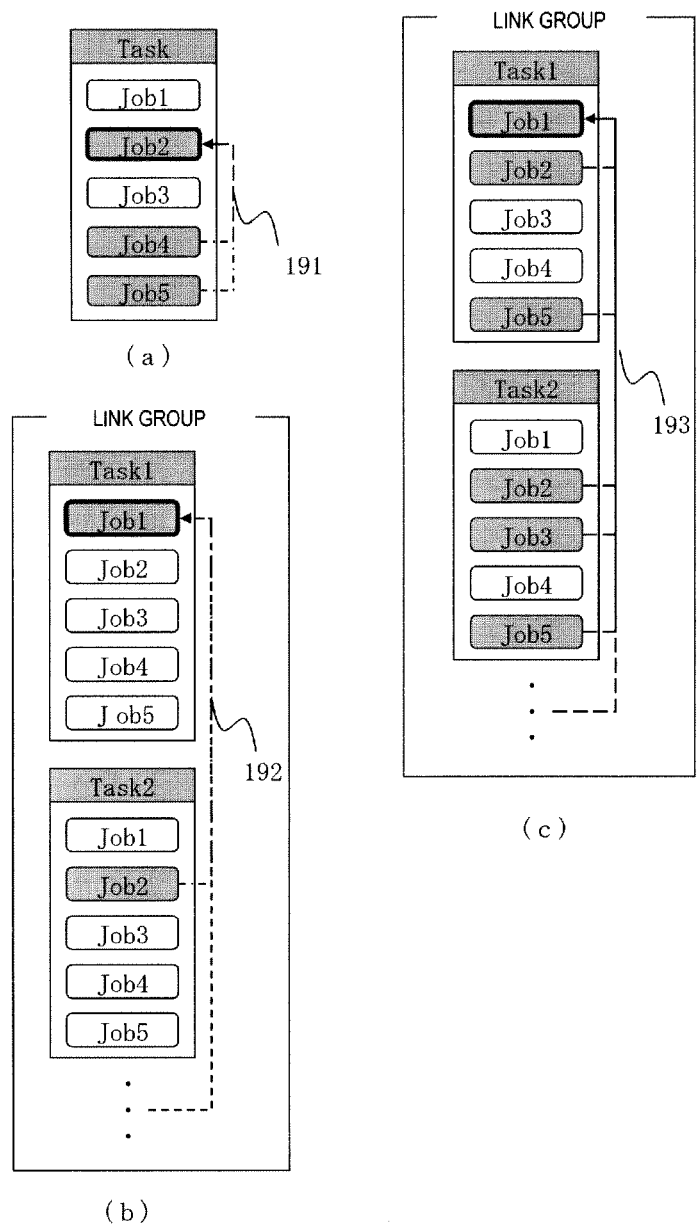
FIG. 19 is a diagram showing a Job link example of the embodiment of the present invention.

FIG. 19 is a diagram showing each link example. FIG. 19(a) shows an example in which the relevant Job group is constructed in one Task, FIG. 19(b) shows an example in which relevant Job groups are constructed beyond Task, and FIG. 19(c) shows an example in which relevant Job groups are constructed by both of intra-Task and inter-Task. In these figures, Jobs connected by dashed lines 191, 192 and 193 are relevant Jobs. In all the figures, when an imaging parameter is changed in a Job surrounded by a heavy frame, the same imaging parameter is changed in all the relevant Job groups.

In each of the above embodiments, the combination "possible or impossible" determination is executed after the imaging "possible or impossible" determination is executed. However, the combination "possible or impossible" determination is not necessarily executed. For example, in an examination that metastatic tumor between distant sites is examined fully, different imaging sites (stations) are imaged by the same imaging sequence. However, it is unnecessary to combine both images. For example, when the parameter check processing is started, it may be configured so as to select the execution of only the imaging "possible or impossible" determination or the execution of both the imaging "possible or impossible" determination and the combination "possible or impossible" determination, and the processing is executed in accordance with the selection.

In each of the above embodiments, the instruction of changing the imaging parameter is received from the user and the parameter check process is executed on all the Jobs in which the imaging parameter is changed. However, they are not limited to this style. For example, separately from the instruction of changing the parameter, the processing may be executed when an instruction of starting the parameter check is accepted. Furthermore, the parameter check may be executed, not on all the Jobs in which the imaging parameter is changed, but on Jobs instructed by the user.

In each of the above embodiments, a process of automatically determining a parameter check target is added to the MRI apparatus, whereby the parameter check of plural Jobs which has been hitherto complicated can be executed in a lump. Furthermore, the combination "possible or impossible" determination of images can be performed before imaging is performed, and thus failure of imaging can be prevented. Furthermore, the change of the imaging parameter is simplified, so that the imaging time can be shortened and the rotation rate of the apparatus can be increased. Moreover, the load on the operator can be reduced.

DESCRIPTION OF REFERENCE NUMERALS AND SIGNS

100 MRI apparatus, 101 examinee, 102 magnetostatic field magnet, 103 gradient magnetic field coil, 104 RF transmission coil, 105 RF reception coil, 106 signal detector, 107 signal processor, 109 gradient magnetic field power source, 110 RF transmitter, 111 controller, 112 bed, 113 bed driving unit, 114 input unit, 115 display unit, 116 storage unit, 300 sequence managing table, 301 JobID, 302 Task name, 303 group name, 304 Job name, 305 imaging sequence type, 700 first error display screen, 701 Task name display area, 702 Job name display area, 703 message display area, 711 second error display screen, 711 Job display area, 712 imaging parameter type display area, 713 cancel button, 1500 first error/suggestion display screen, 1501 Task name display area, 1502 Job name display area, 1503 message display area, 1504 finishing button, 1511 second error/suggestion display screen, 1511 Job display area, 1512 imaging parameter type display area, 1513 suggestion display area, 1514 changing instruction accepting area, 1515 settling instruction accepting area, 1810 common value error display screen, 1811 message display unit, 1812 error information display unit, 1813 button unit, 1820 slice matching error display screen, 1821 message display unit, 1822 error information display unit, 1823 button unit, 1830 OL amount error display screen, 1831 message display unit, 1832 error information display unit, 1833 button unit

The invention claimed is:

1. A magnetic resonance imaging apparatus for performing multistation imaging, characterized by comprising:
    an imaging managing unit that manages imaging executed at each station of the multistation imaging;
    an input unit that accepts an input of an imaging parameter value to be used for the imaging concerned for every imaging managed by the imaging managing unit;
    an imaging "possible or impossible" determining unit that in a case that a new imaging parameter value is input through the input unit, determines with respect to each imaging job or task associated with the new imaging parameter value, whether the new imaging parameter value is proper or improper; and
    an error display unit that displays as an error information (i) identification of an imaging job or task having an imaging parameter value determined to be improper by the imaging "possible or impossible" determining unit and (ii) the imaging parameter value determined to be improper and associated with the identified imaging job or task; and
    a combination "possible or impossible" determining unit that determines whether it is possible or impossible to combine images among stations by using the newly input imaging parameter when there is no imaging parameter value which is determined to be improper by the imaging "possible or impossible" determining unit, wherein when it is determined in the combination "possible or impossible" determining unit that the combination is impossible, the error display unit displays information meaning impossibility of the combination together with information that can specify both adjacent stations to which the combination impossibility is determined,
    wherein the combination "possible or impossible" determining unit comprises:
    a common value determining unit that determines whether an imaging parameter which should have the same value among predetermined imaging operations have the same value among the imaging operations concerned;
    a slice matching determining unit that determines slice matching with respect to imaging in which slices are required to be matched with one another among stations; and
    an overlap determining unit that determines whether an overlap amount between adjacent stations is within a predetermined range with respect to an imaging group in which reconstructed images are combined with one another, wherein when there is an imaging parameter having a different value in imaging parameters determined in the common value determining unit, the error display unit displays the imaging parameter concerned and information that can specify an imaging operation in which the imaging parameter should be identical, when slices are mismatched in the slice matching determining unit, the error display unit displays information that can specify imaging in which mismatching occurs, and when an overlap amount is out of the predetermined range in the overlap unit, the error display unit displays information that can specify both adjacent stations whose overlap amount is out of the range.

2. The magnetic resonance imaging apparatus according to claim 1, wherein the slice matching determining unit executes processing of determining matching of slices when the common value determining unit determines that the imaging parameters have the same value, and the overlap determining unit executes processing of determining whether an overlap amount between the adjacent stations is within a predetermined range when the slice matching determining unit determines that all slices are matched with one another with respect to imaging to which the slice matching is required to be determined.

3. A magnetic resonance imaging apparatus for performing multistation imaging, characterized by comprising:
    an imaging managing unit that manages imaging executed at each station of the multistation imaging;
    an input unit that accepts an input of an imaging parameter value to be used for the imaging concerned for every imaging managed by the imaging managing unit;
    an imaging "possible or impossible" determining unit that in a case that a new imaging parameter value is input through the input unit, determines with respect to each imaging job or task associated with the new imaging parameter value, whether the new imaging parameter value is proper or improper;
    a combination "possible or impossible" determining unit that determines whether it is possible or impossible to combine images among stations by using the newly input imaging parameter; and
    an error display unit that displays at least one of (i) information for enabling specification of an imaging job or task having an imaging parameter value determined to be improper by the imaging "possible or impossible" determining unit and for indicating the imaging parameter value determined to be improper and associated with the imaging job or task, and (ii) information indicating impossibility of combination of images among specific adjacent stations and additional information corresponding to the specific adjacent stations with respect to which the impossibility of the combination of images has been determined,
    wherein the imaging "possible or impossible" determining unit comprises:
    a recommended value calculator that calculates as a recommended value a value nearest to the input imaging parameter value in a permitted range of the imaging parameter value with respect to the imaging parameter value which is determined to be improper; and
    a replacing unit that replaces the imaging parameter value determined to be improper, with the recommended value according to an instruction from an operator, and the error display unit further displays the recommended value.

4. The magnetic resonance imaging apparatus according to claim 3, further comprising an imaging parameter setting unit that sets the new imaging parameter value, input through the input unit, as an imaging parameter to be used for imaging when there is no imaging parameter value which is determined to be improper by the imaging "possibility or impossibility" determining unit.

5. A magnetic resonance imaging apparatus for performing multistation imaging, characterized by comprising:
   an imaging managing unit that manages imaging executed at each station of the multistation imaging;
   an input unit that accepts an input of an imaging parameter value to be used for the imaging concerned for every imaging managed by the imaging managing unit;
   an imaging "possible or impossible" determining unit that in a case that a new imaging parameter value is input through the input unit, determines with respect to each imaging job or task associated with the new imaging parameter value, whether the new imaging parameter value is proper or improper;
   a combination "possible or impossible" determining unit that determines whether it is possible or impossible to combine images among stations by using the newly input imaging parameter; and
   an error display unit that displays at least one of (i) information for enabling specification of an imaging job or task having an imaging parameter value determined to be improper by the imaging "possible or impossible" determining unit and for indicating the imaging parameter value determined to be improper and associated with the imaging job or task, and (ii) information indicating impossibility of combination of images among specific adjacent stations and additional information corresponding to the specific adjacent stations with respect to which the impossibility of the combination of images has been determined,
   wherein the imaging "possible or impossible" determining unit has a replacing unit that calculates a value nearest to the input imaging parameter value in a permitted range of the imaging parameter value with respect to the imaging parameter value which is determined to be improper, and replaces the imaging parameter value by the calculated value.

6. An imaging parameter setting assisting method for setting an imaging parameter value used to perform multistation imaging before execution of the multistation imaging starts, characterized by comprising:
   an input accepting step that accepts an input of a desired imaging parameter value;
   an imaging specifying step that specifies, from all imaging executed in the multistation imaging, imaging in which an imaging parameter value is newly input;
   an imaging "possible or impossible" determining step that determines whether the newly input imaging parameter value is proper or improper with respect to each imaging specified in the imaging specifying step;
   a combination "possible or impossible" determining step that determines whether it is possible or impossible to combine images among stations by using the newly input imaging parameter; and
   a display step that displays at least one of (i) information for enabling specification of an imaging job or task having an imaging parameter value determined to be improper in the imaging "possible or impossible" determining step and for indicating the imaging parameter value determined to be improper and associated with the imaging job or task, and (ii) information indicating impossibility of combination of images among specific adjacent stations and additional information corresponding to the specific adjacent stations with respect to which the impossibility of the combination of images has been determined,
   wherein the imaging "possible or impossible" determining step comprises:
   a recommended value calculation step that calculates as a recommended value a value nearest to the input imaging parameter value in a permitted range of the imaging parameter value with respect to the imaging parameter value which is determined to be improper; and
   a replacing step that replaces the imaging parameter value determined to be improper, with the recommended value according to an instruction from an operator, and the display step further displays the recommended value.

7. An imaging parameter setting assisting method for setting an imaging parameter value used to perform multistation imaging before execution of the multistation imaging starts, characterized by comprising:
   an input accepting step that accepts an input of a desired imaging parameter value;
   an imaging specifying step that specifies, from all imaging executed in the multistation imaging, imaging in which an imaging parameter value is newly input;
   an imaging "possible or impossible" determining step that determines whether the newly input imaging parameter value is proper or improper with respect to each imaging specified in the imaging specifying step;
   a combination "possible or impossible" determining step that determines whether it is possible or impossible to combine images among stations by using the newly input imaging parameter; and
   a display step that displays at least one of (i) information for enabling specification of an imaging job or task having an imaging parameter value determined to be improper in the imaging "possible or impossible" determining step and for indicating the imaging parameter value determined to be improper and associated with the imaging job or task, and (ii) information indicating impossibility of combination of images among specific adjacent stations and additional information corresponding to the specific adjacent stations with respect to which the impossibility of the combination of images has been determined,
   wherein the imaging "possible or impossible" determining step includes a replacing step that calculates a value nearest to the input imaging parameter value in a permitted range of the imaging parameter value with respect to the imaging parameter value which is determined to be improper, and replaces the imaging parameter value by the calculated value.

* * * * *